United States Patent
Morrissey et al.

(10) Patent No.: US 6,303,596 B1
(45) Date of Patent: Oct. 16, 2001

(54) USE OF TAUROLIDINE FOR TREATMENT OF LEUKEMIAS

(75) Inventors: James H. Morrissey, Oklahoma City, OK (US); Anne Hamik, Baltimore, MD (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/424,426

(22) PCT Filed: May 22, 1998

(86) PCT No.: PCT/US98/10494

§ 371 Date: Mar. 1, 2000

§ 102(e) Date: Mar. 1, 2000

(87) PCT Pub. No.: WO98/52572

PCT Pub. Date: Nov. 26, 1998

Related U.S. Application Data

(63) Continuation of application No. PCT/US98/10494, filed on May 22, 1998.
(60) Provisional application No. 60/047,642, filed on May 22, 1997.

(51) Int. Cl.[7] .................................................. A61K 31/54
(52) U.S. Cl. ........................................................... 514/222.5
(58) Field of Search .......................................... 514/222.5

(56) References Cited

U.S. PATENT DOCUMENTS 5,593,665  1/1997  Pfirrmann et al. .................. 424/85.1

OTHER PUBLICATIONS

Arends, M.J. and Wyllie, A.H., "Apoptosis: mechanisms and roles in pathology," *Int Rev Exp Path* 32:223–254 (1991).
Bauer, et al., "Tissue factor gene expression in acute myeloblastic leukemia," *Thromb Res* 56:425–430 (1989).
Bedrosian, et al., "Taurolidine, an analogue of the amino acid taurine, suppresses interleukin 1 and tumor necrosis factor synthesis in human peripheral blood mononuclear cells," *Cytokine* 3:568–575 (1991).
Billing, A., et al., "The influence of taurolin on defense functions and bacterial growth in human peritonitis," *Langenbecks Arch. Chir.* 377:180–185 (1992).
Boyle, et al., "Apoptosis in C3H–10T1/2 cells: role of intracellular pH, protein kinase C, and the Na+/H+ antiporter," *J. Cell Biochem* 67:231–240 (1997).
Browne, M.K., "*Staphylococcus septicaemia* case report," In *Taurolin, Ein Neues Konzept zur Antimikrobiellen Chemotherpie Chirurgischer Infektionen*, Bruchner, W.L. and Pfirrmann, R.W. (eds), Muchen—61–63. Wein–Baltimore, Urban & Schwarzenberg, p. 61–63, 1985.
Browne, M.K., et al., "A controlled trial of taurolin in established bacterial peritonitis," *Surg Gynecol Obstet* 146:721–724 (1978).
Browne, M.K., "Pharmacological and clinical studies with taurolin." In *Taurolin, Ein Neues Konzept zur Antimikrobiellen Chemotherpie Chirurgischer Infektionen*, Bruchner, W.L. and Pfirrmann, R.W. (eds), Muchen–Wein–Baltimore, Urban & Schwarzenberg, p.51–60, 1985.
Browne, M.K., et al., "Taurolin, a new chemotherapeutic agent," *J. Appl. Bacter.* 41:363–368 (1976).
Chand, N., et al., "Disease modifying activity to taurolin in adjuvant–induced arthritis in rats," *Pharmacologist*, 34(3):205; abstract #376 (1992).
Darzynkiewicz, et al., "Assays of cell viability: discrimination of cells dying by apoptosis," *Methods Cell Biol* 41:15–38 (1994).
Dofferhoff, et al., "The release of endotoxin from antibiotic–treated *Escherichia coli* and the producion of tumour necrosis factor by human monocytes," *J Antimicrob Chemother* 31:373–384 (1991).
Evans, et al., "Activation of the Abelson tyrosine kinase activity is associated with suppression of apoptosis in hemopoietic cells," *Cancer Res* 53:1735–1738 (1993).
Gansauge, et al., "The induction of apoptosis in proliferating human fibroblasts by oxygen radicals is associated with a p53– and $p21^{WAF1CIP1}$ induction," *FEBS Letters* 404:6–10 (1997).
Gavriali, et al., "Identification of programmed cell death in situ via specific labeling of nuclear DNA fragmentation," *J Cell Biol* 119:493–501 (1992).
Gorman, et al., "Reduced adherence of microorganisms to human mucosal epithelial cells following treatment with taurolin, a novel antimicrobial agent," *J Appl Bacteriol* 62:315–320 (1987).
Gregory, et al., "Regulation of tissue factor gene expression in the monocyte procoagulant response to endotoxin," *Mol Cell Biol* 9:2752–2755 (1989).
Hair, et al., "Tissue factor expression in human leukemia cells," *Leuk Res* 20:1–11 (1996).
Harrison, J.E., et al., "Anti–inflammatory activity of taurolin," *Pharmacologist*, 34(3):205, abstract #377 (1992).
Helsinki, et al., "Long–term cultivation of functional human macrophages in teflon dishes with serum–free media," *J Leuk Biol* 44:111–121 (1998).
Houston, et al., "Endothelial cells and extracellular calmodulin inhibit monocyte tumor necrosis factor release and augment neutrophil elastase release," *J Biol Chem* 273:11778–11785 (1997).
Itoh, et al., "The polypeptide encoded by the cDNA for human cell surface antigen Fas can mediate apoptosis," *Cell* 66:233–243 (1991).
Iwai, K., et al., "Differential expression of bcl–2 and susceptibility to anti–Fas—mediated cell death in peripheral. blood lymphocytes, monocytes, and neutrophils," *Blood* 84:1201–1208 (1994).

(List continued on next page.)

Primary Examiner—Jerome D. Goldberg
(74) Attorney, Agent, or Firm—Kevin B. Clarke

(57) ABSTRACT

The invention relates to selective induction of cell death by apoptosis and applicability to treatment of leukemias.

13 Claims, 15 Drawing Sheets

OTHER PUBLICATIONS

Johnston, D.A., et al., "Taurolin for the prevention of parenteral nutrition related infection: antimicrobial activity and long–term use," *Clinical Nutrition,* 12:365–368 (1993).

Jones, et al., "A study of the stability of taurolidine also reduces the protein–free serum," *Int J Pharm* 64:R1–R4 (1990).

Kerr, J.F.R., et al., "Apoptosis: Its significance in cancer and cancer therapy," *Cancer,* 73(8): 2013–2026 (1994).

Kim, et al., "Platelet–derived growth factor induces apoptosis in growth–arrested murine fibroblasts," *Proc Natl Acad Sci USA* 92:9500–9504 (1995).

Kochi, S.K. and Collier, R.J., "DNA fragmentation and cytolysis in U937 cells treated with diptheria toxin or other inhibitors of protein synthesis," *Exp Cell Res* 208:296–302 (1993).

Kyprianou, et al., "Programmed cell death during regression of the MCF–7 Human Breast Cancer following estrogen ablation," *Cancer Research,* 51:162–166 (1991).

Levi, et al., "Inhibition of endotoxin–induced activation of coagulation and fibrinolysis by pentoxifylline or by a monoclonal anti–tissue factor antibody in chimpanzees," *J Clin Invest* 93:114–120 (1994).

Liao, et al., "Stress, apoptosis, and mitosis induce phosphorylation of human keratin 8 at Ser–73 in tissues and cultured cells," *J Biol Chem* 272:17565–17573 (1997).

Lowe, S.W., et al., "p53 status and the efficacy of cancer therapy in vivo," *Science,* 266:807–810 (1994).

Lucarotti, M., et al., "Antiseptic toxicity to breast carcinoma in tissue culture: an adjuvant to conservation therapy?" *Annals of the Royal College of Surgeons of England,* 72:388–392 (1990).

Mangan, et al., "Lipopolysaccharide, tumor necrosis factor–α, and IL–1β prevent programmed cell death apoptosis) in human peripheral blood monocytes," *J Immunol* 146:1541–1546 (1991).

Mangan, D.F. and Wahl, S.M., "Differential regulation of human monocyte programmed cell death (apoptosis) by chemotactic factors and pro–inflammatory cytokines," *J Immunol* 147:3408–3412 (1991).

Mangan, et al., "IL–4 enhances programmed cell death (apoptosis) in stimulated human monocytes," *J Immunol* 148:1812–1816 (1992).

Martin, et al., "Biochemical modulation of tumor cell energy in vivo: II. A lower dose of adrimycin is required and a greater antitumor activity is induced when cellular energy is depressed," *Cancer Investigation,* 12(3):296–307 (1994).

McCartney, A.C. and Browne, M.K., "Clinical studies on administration of taurolin in severe sepsis: a preliminary study," *Bacterial Endotoxins: Pathophysiological Effects, Clinical Significance, and Pharmacological Control,* pp. 361–371 (1988).

Monson, J.R.T., et al., "Taurolidine as an anti–neoplastic agent: a previously undiscovered role?" *Br. J. Surg.,* vol. 77, No. 12, p. 1433 (1990).

Monson, et al. "Taurolidine inhibits tumour necrosis factor (TNF) toxicity—new evidence of TNF endotoxin synergy," *Eur J Surg Oncol* 19:226–231 (1993).

Nitsche, et al., "Investigations of endotoxin inactivation in plasma. Preliminary results of a controlled randomized study on taurolidine as a supplementary therapeutic agent in septicemia." In *Emergency Surgery Trends, Techniques, Results.* Proceedings of the $7^{th}$ International Congress of Emergency Surgery, Schweiberer, L. and Eitel, F. (eds), Munich, Zuckschwerdt, p. 185–188, 1985.

Pfirrmann, R.W. and Leslie, G.B., "The anti–endotoxin activity of taurolin in experimental animals," *Journal of Applied Bacteriology,* 46:97–102 (1979).

Pfirmann, R.W., "Taurolin: ein neues konzept zur antimikrobiellen chemotherpie chirurgischer infektionen einfurhrung und ubersicht." In *Taurolin: Ein Neues Konzept zur Antimikrobiellen Chemotherpie Chirurgischer Infektionen,* Bruchner, W.L. and Pfirrmann, R.W. (eds), Muchen–Wein–Baltimore, Urban & Schwarzenberg, p. 3–23, 1985.

Polverino, A.J. and Patterson, S.D., "Selective activation of caspases during apoptotic induction in HL–60 cells," *J Biol Chem* 272:7013–7021 (1997).

Rezaie, et al., "Expression and purification of a soluble tissue factor fusion protein with an epitope for an unusual calcium–dependent antibody," *Protein Expression and Purification* 3:453–460 (1992).

Sachs, L. and Lotem, J., "Control of programmed cell death in normal and leukemic cells: new implications for therapy," *Blood,* 82(1):15–21 (1993).

Schwartz, et al., "Murine lymphoid procoagulant activity induced by bacterial lipopolysaccharide and immune complexes is a monocyte prothrombinase," *J Exp Med* 155:1464–1479 (1982).

Sen, S. and D'Incalci, M., "Biochemical events and relevance to cancer chemotherapy," *FEBS,* 307(1):122–127 (1992).

Tanaka, M. and Yamanishi, H., "The expression of tissue factor antigen and activity on the surface of leukemic cells," *Leuk Res* 17:103–111 (1993).

Taylor, et al., "Lethal *E. coli* septic shock is prevented by blocking tissue factor with monoclonal antibody," *Circ Shock* 33:127–134 (1991).

Thomae, K., "Taurolidine, *Drugs of the Future*" 14:237–238 (1989).

Ulevitch, R.J. and Tobias, P.S., "Recognition of endotoxin by cells leading to transmembrane signaling," *Curr Opin Immunol* 6:125–130 (1994).

Watson, et al., "Taurolidine, an antilipopolysaccharide agent, has immunoregulatory properties that are mediated by the amino acid taurine," *J Leuk Biol* 58:299–306 (1995).

Willatts, S.M., et al., "Effect of the antiendotoxic agent, taurolidine, in the treatment of sepsis syndrome: A placebo–controlled, double–blind trial," *Critical Care Medicine,* vol. 23, No. 6:1033–1039 (1995).

Wyllie, A.H., et al., "Cell death: the significance of apoptosis," *International Review of Cytology,* 68:251–306 (1980).

Ziegler–Heitbrock, H.W.L., et al. "Establishment of a human cell line (mono mac 6) with characteristics of mature monocytes," *Int. J. Cancer,* 41:456–461 (1988).

USE OF TAUROLIDINE FOR TREATMENT OF LEUKEMIAS

CROSS REFERENCE TO RELATED APPLICATION

This application claims the benefit of prior filed copending U.S. Provisional Application No. 60/047,642 filed May 22, 1997 and is a 371 of PCT/U.S. Ser. No. 98/10494, filed May 22, 1998.

BACKGROUND OF THE INVENTION

Cell death proceeds by one of two mechanisms: necrosis or apoptosis. In necrosis, the cells lyse and cytosolic components are released. The released cytosolic components elicit severe inflammatory responses. Apoptosis does not result in the release of cytosolic contents, as the cell membrane remains intact even though its surface properties may change. Apoptosis may include the break up of cells into apoptotic bodies, spherical pieces of cells in which the membrane still prevents the release of cytosolic contents. Apoptotic cells and apoptotic bodies are removed in the body by phagocytic cells which are believed to recognize the need to remove such cells by the changes in the outer leaflet of the membrane, in which phosphatidylserine is exposed. Apoptosis typically does not provoke inflammatory responses the way necrosis does because in the former case, the cells are removed by phagocytosis before the cytosolic content is released.

Although cells undergoing apoptosis in vitro initially have intact cell membranes, cells in advanced stages of apoptosis can exhibit loss of membrane integrity. This process is sometimes called "secondary necrosis." It can be observed owing to the absence of phagocytic cells, which in vivo would have removed the apoptotic cells and cell fragments before they could become necrotic.

When neoplastic (tumor) cells are present in the body, it is desirable to cause the death of such cells without causing the death of the normal cells which the patient needs to sustain his life. It is desirable to cause the death of neoplastic cells by inducing apoptosis, so that the cytosolic contents of the neoplastic cells are not released.

Antineoplastic drugs have been reported which kill tumor cells by inducing apoptosis. While some of these drugs have been successful in treating some types of cancer, the drugs have also been known to induce severe side effects, such as cytotoxicity to normal cells by interference with basic cellular functions such as protein synthesis or DNA replication. A few inducers of apoptosis in monocytes have been reported. For example, human blood monocytes can undergo apoptosis when cultured in the absence of serum or stimulatory factors (which is impossible to achieve in vivo). Mangan, et al., "Lipopolysaccharide, tumor necrosis factor-α, and IL-1β prevent programmed cell death (apoptosis) in human peripheral blood monocytes," *J Immunol* 146:1541 (1991). This process takes two to three days for approximately 50% of the monocytes to become apoptotic (Mangan, et al., "IL-4 enhances programmed cell death (apoptosis) in stimulated human monocytes," *J Immunol* 148:1812 (1992)), and apoptosis can be postponed by lipopolysaccharide (LPS), interleukin (IL)-1, and α-tumor necrosis factor (TNFα). In addition, the anti-inflammatory cytokine IL-4 can enhance apoptosis in LPS-stimulated monocytes. Mangan, D. F. and Wahl, S. M., "Differential regulation of human monocyte programmed cell death (apoptosis) by chemotactic factors and pro-inflammatory cytokines," *J Immunol* 147:3408–3412(1991). Apoptosis has also been induced in several different cell types by the use of a number of cytokines. However, the potential use of cytokines for treatment of cancer in vivo has suffered from drawbacks, since they have been reported to elicit a variety of deleterious effects, including shock, circulatory collapse and death. In addition, the manufacture of cytokines has been to date, complicated and expensive since recombinant technology for manufacturing proteins is not an inexpensive proposition on a large scale basis.

Further adding to the complicated nature of leukemia treatment is the fact that there are many different types of leukemia. In viewing the scheme of hemopoiesis, pluripotent stem cells divide to form either lymphoid stem cells or myeloid stem cells. Lymphocytes are produced from lymphoid stem cells, while monocytes and granulocytes such as neutrophils, eosinophils and basophils are produced from myeloid stem cells. Myeloid stem cells also give rise to erythrocytes and megakaryocytes. Various leukemias resulting from these differentiated cells include lymphocytic leukemia, monocytic leukemia, and myeloid leukemia. Treatment methodologies and prognosis differ depending on the specific type of leukemia.

Particularly difficult to treat are myeloid and monocytic leukemias. Current treatment methods have achieved palliation and not cure. For example, patients having monocytic leukemia are generally thought to have a low cure rate of less than ten percent. A true remission is impossible to achieve because the Ph-positive clone persists in the bone marrow, and intense chemotherapy treatments designed to eliminate or reduce the clone have only provided modest improvements in the length of survival of these patients. Current chemotherapy is designed to keep the patient asymptomatic for long periods of time by maintaining a total white blood count within an acceptable range.

It is, therefore, desirable to find a new agent that could selectively cause apoptosis of monocytic, myeloid, and leukemia cells without causing severe side effects that accompany the administration of traditional chemotherapeutic agents. It has now been found that a known composition, taurolidine, can be used for the induction of apoptosis in monocytic and myeloid cells.

BRIEF DESCRIPTION OF THE DRAWINGS

FIG. 2A represents MM6 cells; FIG. 2B represents PBMC. The cells were induced with LPS (hatched bars: 100 ng/ml LPS in RPMI supplemented with 10% BCS (RPMI+10% BCS); solid bars: 10 ng/ml in AIM-V+0.01% BCS) in the presence of varying concentrations of taurolidine, or with a dilution of the vehicle equivalent to that given to cells receiving 100 μg/ml taurolidine. After four hours, cells were collected and lysates were prepared for TF ELISA. Data are expressed as percent of TF antigen measured in cells treated with LPS alone (no taurolidine or vehicle). Experiments were performed with duplicate samples and were repeated at least three times. Values shown are mean±SEM of all experiments.

FIG. 3A represents MM6 cells; FIG. 3B represents PBMC. The cells were induced with LPS (hatched bars: 100 ng/ml LPS in RPMI+10% BCS; solid bars: 10 ng/ml in AIM-V+0.01% BCS) in the presence of varying concentrations of taurolidine. After four hours, cell supernatants were collected for TNFα ELISA. Data are expressed as percent of TNFα levels measured in cell cultures treated with LPS alone (no taurolidine or vehicle). Experiments were performed with duplicate samples and were repeated at least three times. Values shown in FIG. 3A are from a representative experiment. Values shown in FIG. 3B are mean±SEM of three experiments.

FIG. 12A represents untreated MM6 cells; FIG. 12B represents MM6 cells treated with 50 µg/ml taurolidine; FIG. 12C represents untreated PBMC; and FIG. 12D represents PBMC treated with 75 µg/ml taurolidine. M=monocytes; L=lymphocytes.

DETAILED DESCRIPTION

Figure 1:
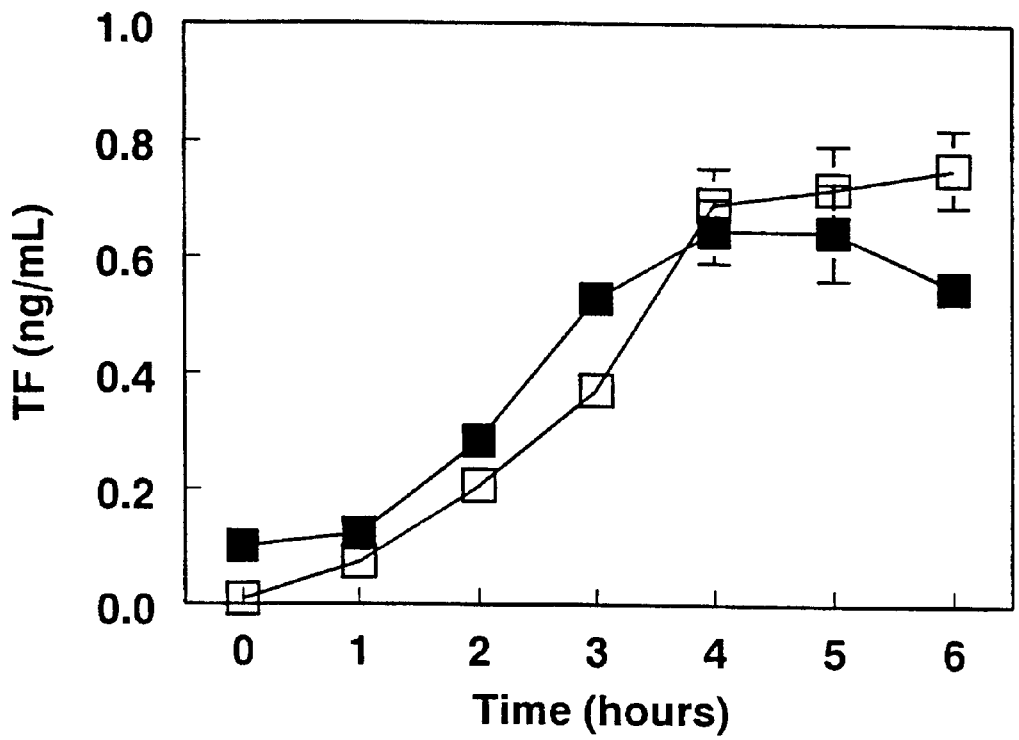
FIG. 1 is a graph depicting the expression of tissue factor (TF) by lipopolysaccharide (LPS)-stimulated peripheral blood mononuclear cells (PBMC) and Mono Mac 6 (MM6) cell line. PBMC at $1.5 \times 10^7$ cells/ml (open squares), or $5.6 \times 10^5$ cells/ml (closed squares) were cultured in AIM-V supplemented with 0.01% bovine calf serum (AIM-V+ 0.01% BCS). After treatment with 10 ng/ml LPS, samples were collected for ELISA at the indicated times. Data (mean±SD from samples assayed in quadruplicate) are from a representative experiment. In this experiment, uninduced MM6 cells expressed 160 pg TF per $1 \times 10^6$ cells, while induced PBMC expressed less than 1 pg TF per $1 \times 10^6$ cells.

Taurolidine (taurolin; tauroline; 4,4'-methylenebis (perhydro-1,2,4-thiadiazin 1,1-dioxide) is disclosed for the first time as an agent for treating patients inflicted with monocytic and/or myeloid leukemias. Taurolidine is administered by injection in solution (intravenously or intraperitoneally) to afflicted patients in an amount effective to cause apoptosis of monocytic and/or myeloid cells. The cells involved in the monocytic or myeloid leukemia disease are thus attacked and die via apoptosis.

Taurolidine has been reported as a useful agent for other applications, and thus, in vitro and clinical data is available on its physiological effects, even though there are no previous reports on its use as an apoptosis-inducer in monocytes, granulocytes, or leukemia cells. No toxic effects on epithelial cells were reported after two hour treatment with 5 mg/ml taurolidine, (Gorman, et al., "Reduced adherence of microorganisms to human mucosal epithelial cells following treatment with taurolin, a novel antimicrobial agent," *J Appl Bacteriol* 62:315 (1987)), and previous studies on monocytes reported that taurolidine was apparently non-toxic since there was no increase in LDH release by cells after 24-hour taurolidine treatment. Bedrosian, et al., "Taurolidine, an analogue of the amino acid taurine, suppresses interleukin 1 and tumor necrosis factor synthesis in human peripheral blood mononuclear cells," *Cytokine* 3:568 (1991); Dofferhoff, et al, "The release of endotoxin from antibiotic-treated *Escherichia coli* and the production of tumor necrosis factor by human monocytes," *J Antimicrob Chemother* 31:373 (1991).

In previous reports on other applications of taurolidine, such as for an agent to address septicemia, plasma concentrations of taurolidine (or its initial metabolite) achieved in clinical use range from 20 to 100 µg/ml in septic patients or normal volunteers. Browne, M. K., "Pharmacological and clinical studies with taurolin." In *Taurolin, Ein Neues Konzept zur Antimikrobiellen Chemotherapie Chirurgischer Infektionen*, Brückner, W. L. and Pfirrmann, R. W. (eds), M ünchen-Wien-Baltimore, Urban & Schwarzenberg, p. 3, 1985; Nitsche, et al., "Investigations of endotoxin inactivation in plasma. Preliminary results of a controlled randomized study on taurolidine as a supplementary therapeutic agent in septicemia." In *Emergency Surgery Trends, Techniques, Results. Proceedings of the 7th International Congress of Emergency Surgery*, Schweiberer, L. and Eitel, F. (eds), Munich, Zuckschwerdt, p.185, 1985). Taurolidine treatment in humans has not been associated with toxicity, even when septic patients have received up to 20 grams for 2–5 consecutive days. Willatts, et al., "Effect of the antiendotoxic agent, taurolidine, in the treatment of sepsis syndrome: a placebo-controlled double-blind trial," *Crit Care Med* 23:1033 (1995); Johnston, et al., "Taurolin for the prevention of parenteral nutrition related infection: antimicrobial activity and long-term use," *Clin Nutrition* 12:365 (1993).

It has been found that concentrations of taurolidine in the range of 50 to 100 μg/ml induced apoptosis in 75% of peripheral blood monocytes incubated in culture medium within six hours. Further, 100 μg/ml taurolidine induced apoptosis in 92% of granulocytes incubated in culture medium within six hours. Preferred therapeutic dosages for treatment of leukemias are from about 10 to about 500 mg/kg body weight. Most preferred is a dose that results in a 200 μg/ml concentration in the plasma, which is typically about 150 mg/kg body weight.

Taurolidine can be administered intravenously or intraperitoneally. For treatment of the various leukemias, an effective amount of taurolidine to cause apoptosis of the affected cells is used and can be monitored by periodic tests on samples of the patient's blood where cells can be observed for evidence of apoptosis using any technique such as TUNEL analysis, DNA fragmentation, or with other suitable markers of apoptosis.

In our studies, taurolidine was used in the form of a 2% w/v solution in a vehicle containing 2% dextrose and 5% polyvinylpyrrolidone. A solution consisting of the vehicle alone was obtained from Wallace Laboratories (Cranbury, N.J.) for the preparation of a vehicle control. Reagents and supplies were obtained as follows: Histopaque, propidium iodide (PI), Lactate Dehydrogenase (LDH) Kit, rabbit brain thromboplastin, anisomycin, and dimethylsulfoxide (DMSO) from Sigma Chemical Co. (St. Louis, Mo.); 6% dextran 70 in 0.9% NaCl (6% dextran) from McGaw, Inc. (Irvine, Calif.); RPMI, Eagle's minimum essential medium (MEM), and Hank's balanced salt solution (HBSS) from Mediatech, Inc. (Herdon, Va.); medium M199 from Bio Whittaker, Inc., (Walkersville, Md.); bovine calf serum (BCS) from HyClone Laboratories, Inc. (Logan, Utah.); 25% human serum albumin (HSA) from the American Red Cross Blood Services (Washington, D.C.); AIM-V medium from Gibco BRL (Grand Island, N.Y.); LPS (*E. coli* 0111:B4) and bovine serum albumin (fatty acid free) from Calbiochem Corp. (La Jolla, Calif.); FITC-conjugated anti-CD14 antibodies, FITC-conjugated anti-CD3/PE-conjugated anti-CD19 Simultest, and PE-conjugated anti-CD16 from Becton Dickinson (Parsippany, N.J.); and the TUNEL assay system (In Situ Cell Death Detection Kit) from Boehringer Mannheim (Indianapolis, Ind.).

Numerous cell lines have been examined and are listed in Table I. MM6 cells, derived from the peripheral blood of a patient with acute monoblastic leukemia (M5), were a generous gift of Dr. H. Ziegler Heitbrock. The K562 cell line, developed from cells from pleural fluid of a patient with chronic myeloid leukemia in blast crisis, was obtained from the American Type Culture Collection (ATCC) (Rockville, Md.). K562 cells can be induced to differentiate into precursors of the monocytic, granulocytic, and erythrocytic series. HL-60 cells, established from peripheral blood leukocytes of a patient with acute promyelocytic leukemia, were obtained from ATCC. HL-60 cells display surface receptors and react with cytochemical stains specific for granulocytic cells. REH cells, originated from acute lymphoblastic leukemia cells, were obtained from ATCC. REH cells have a non-T, non-B phenotype. Jurkat is a human leukemic T cell line available from ATCC. ECV304, a spontaneously transformed immortal endothelial cell line derived from a human umbilical cord, was obtained from

TABLE I

Cell Lines Tested

| Human Cell Line | Derived from a Patient with |
| --- | --- |
| HL-60 | acute myeloid leukemia |
| K-562 | chronic myelogenous leukemia |
| Mono Mac 6 | monocytic leukemia |
| REH | acute lymphocytic leukemia |
| Jurkat | human leukemic T cell line |
| ECV304 | human endothelial cell line (spontaneously transformed) |
| GM5387 | human fetal fibroblast cell line |

ATCC. The human fibroblast cell line GM5387, derived from tissue obtained by fetal lung biopsy, was obtained from NIGMS Human Genetic Mutant Cell Repository.

All cells were cultured in a 5% $CO_2$ atmosphere at 37° C. MM6 cells were grown in RPMI supplemented with 10% BCS, 2 mM L-glutamine, and 50 μg/ml gentamicin (RPMI+ 10% BCS). In some experiments, MM6 cells were rinsed once with HBSS without $Ca^{++}$ or $Mg^{++}$ and once with AIM-V before finally being resuspended in AIM-V supplemented with 0.01% BCS (AIM-V+0.01% BCS). AIM-V has been shown to support long-term culture of macrophages (Helsinki, et al., "Long-term cultivation of functional human macrophages in teflon dishes with serum-free media," *J Leuk Biol* 44:111 (1988)), and in the present experiments, MM6 cells cultured in AIM-V for at least ten days maintained high viability and exhibited growth rates only slightly slower than cells grown in RPMI supplemented with 10% BCS. AIM-V was supplemented with a low amount of BCS (0.01%) in order to provide a source of LPS-binding protein, which enhances the response of monocytic cells to LPS. Ulevitch, R. J. and Tobias, P. S., "Recognition of endotoxin by cells leading to transmembrne signaling," *Curr Opin Immunol* 6:125 (1994). HL-60, REH, and Jurkat were cultured in RPMI supplemented with 10% heat inactivated fetal bovine serum (FBS), 2 mM L-glutamine, and 50 μg/ml gentamicin. ECV304 were cultured in M199 supplemented with 10% FBS, mM L-glutamine, and 50 μg/ml gentamicin. GM5387 was cultured in MEM supplemented with 20% FBS, 2 mM L-glutamine, and 50 μg/ml gentamicin.

Human peripheral blood mononuclear cells (PBMC) were isolated from heparinized blood by centrifugation using Histopaque as per manufacturer's instructions. The isolated PBMC were suspended in RPMI supplemented with 10% BCS and were used in experiments immediately thereafter. As determined by flow cytometry, PBMC were typically 11±2% monocytes and 80±13% lymphocytes, with the remaining cytometric events consistent in size with platelets and cell aggregates.

Human granulocytes were isolated from heparinized blood by diluting blood 1:1 with 6% dextran to sediment RBC, then centrifuging to obtain leukocyte rich plasma. The remaining RBC were lysed by 20 second incubation with 0.2% NaCl. After lysis, NaCl was added to a final concentration of 0.9%, the sample was centrifuged, and the cell pellet resuspended in HBSS containing 0.5% HSA. An equal volume of Histopaque (Sigma) was layered underneath the cell suspension. Upon centrifugation, the PBMC remained above the Histopaque layer, while the granulocytes were sedimented. Purity of collected granulocytes was assayed by flow cytometry using PE-conjugated anti-CD19.

Tissue Factor and TNFα Expression

The induction of tissue factor (TF) expression by bacterial LPS was demonstrated in numerous cell lines including human peripheral blood mononuclear cells, human monocytic cell line Mono Mac 6 (MM6), and granulocytes. The induction of tissue factor expression was blocked by treatment with taurolidine.

For induction of TF or TNFα expression, MM6 cells or PBMC were cultured either in RPMI supplemented with 10% BCS or in AIM-V+0.01% BCS, and stimulated by adding LPS to final concentrations of 10 to 100 ng/ml. Cells treated with taurolidine received final concentrations of 10 to 100 μg/ml taurolidine, with parallel cultures receiving either no taurolidine or a comparable dilution of the vehicle alone. Except as noted, taurolidine and LPS were added to the cell cultures simultaneously. For TF determination, cells and culture media together were treated by adding Triton X-100 (1% final) and EDTA (7 mmol/L final), and the resulting lysates assayed by ELISA. Rezaie, A. R., et al., "Expression and purification of a soluble tissue factor fusion protein with an epitope for an unusual calcium-dependent antibody," *Protein Expression and Purification* 3:453 (1992). For TNFα determination, cells were removed by centrifugation for 5 min at 250×g, and the supernatants were assayed by ELISA. Houston, et al., "Endothelial cells and extracellular calmodulin inhibit monocyte tumor necrosis factor release and augment neutrophil elastase release," *J Biol Chem* 272:11778–11785 (1997). In order to examine if taurolidine interfered with ELISA measurement of TF, taurolidine was added to lysates of cells that had previously not been treated with the drug. Taurolidine had no effect on the measurement of TF levels.

A number of previous studies have shown that peripheral blood monocytes respond to LPS stimulation by expressing TF, with maximal expression typically occurring four to six hours after LPS treatment. Schwartz, et al, "Murine lymphoid procoagulant activity induced by bacterial lipopolysaccharide and immune complexes is a monocyte prothrombinase," *J Exp Med* 155:1464 (1982); Gregory, et al., "Regulation of tissue factor gene expression in the monocyte procoagulant response to endotoxin," *Mol Cell Biol* 9:2752 (1989). Furthermore, monocytes are the only cell type present in PBMC preparations that are capable of expressing TF. When cultured in AIM-V+0.01% BCS, MM6 cells and PBMC responded in a similar fashion to LPS stimulation (FIG. 1). For MM6 cells, maximal TF expression was achieved with 10 ng/ml LPS, resulting in an 11-fold induction of TF expression compared to unstimulated cells. For PBMC, maximal TF expression was >30-fold higher than in unstimulated cells. When MM6 cells were cultured in RPMI+10% BCS, similar time courses of LPS-induced TF expression were observed, although maximal induction of TF expression was achieved with 100 ng/ml LPS, resulting in a 4.3-fold induction of TF expression compared to unstimulated cells.

Figure 2A:
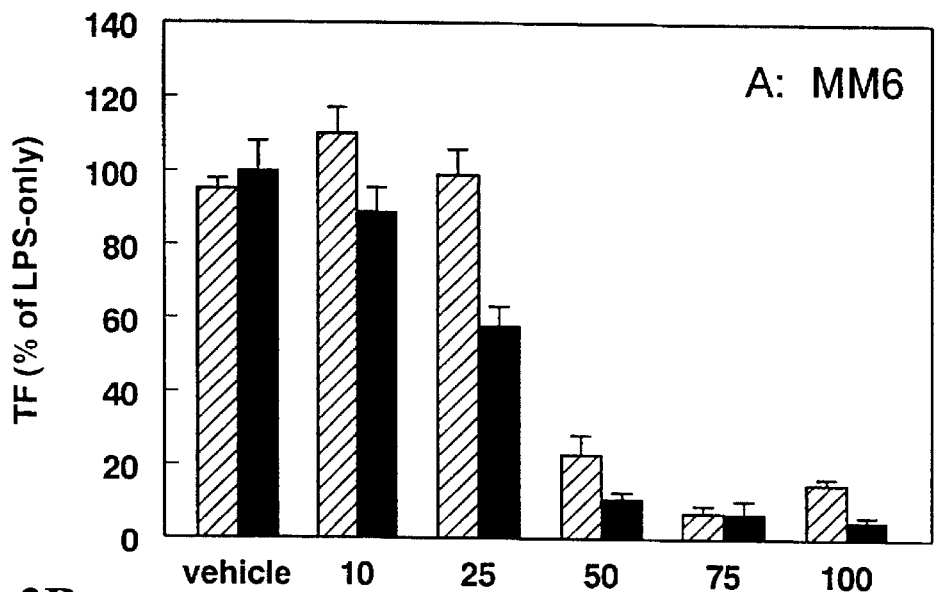
FIG. 2A and FIG. 2B are graphs depicting taurolidine inhibition of LPS-induced TF expression by monocytic cells as determined by assay procedures.
Figure 2B:
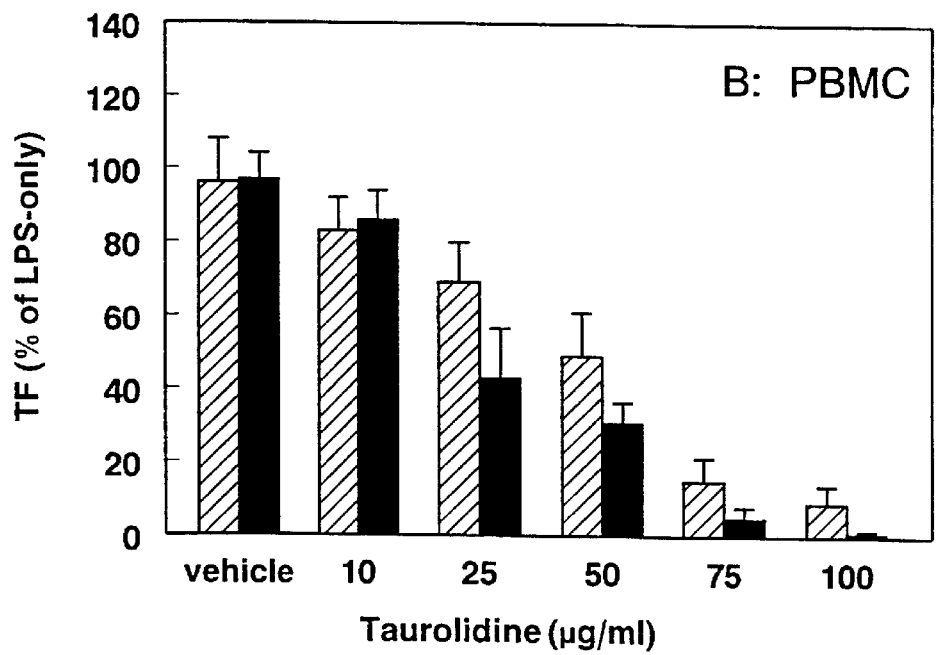

The ability of taurolidine to inhibit LPS-induced TF expression in MM6 and PBMC was examined. Taurolidine at concentrations of 50 μg/ml or higher completely blocked the induction of TF expression in MM6 cells by LPS, while vehicle alone (used at a dilution comparable that of 100 μg/ml taurolidine) had no effect (FIG. 2A). Lower concentrations of taurolidine (10 or 25 μg/ml) had little or no effect on TF expression by MM6 cells. TF expression by LPS-stimulated PBMC was also inhibited by taurolidine (FIG. 2B), although slightly higher concentrations were required (i.e., 75 μg/ml taurolidine was required for complete inhibition of TF expression, compared with 50 μg/ml for MM6 cells). Taurolidine exhibited similar effectiveness in blocking TF expression when MM6 cells or PBMC where cultured in either RPMI+10% BCS or in AIM-V+0.01% BCS.

Some of the immunomodulatory effects of taurolidine have been proposed to result from its breakdown product, taurine. William, et al., "Taurolidine, an antilipopolysaccharide agent, has immunoregulatory properties that are mediated by the amino acid taurine," *J Leuk Biol* 58:299(1995). Therefore, in order to examine this potential mechanism of action of taurolidine, we performed experiments as above using taurine at 44 μg/ml (equivalent in molar concentration to that which would be generated from the complete breakdown of 50 μg/ml taurolidine) and higher. Taurine had no effect on TF expression by MM6 cells, even at concentrations up to 0.5 mg/ml. Another proposed mechanism of action of taurolidine is via direct inactivation of LPS. Pfirrnann, R. W., "Taurolin: ein neues konzept zur antimikrobiellen chemotherapie chirurgischer infecktionen einf ürhrung und iübersicht." In *Taurolin, Ein Neues Konzept zur Antimikrobiellen Chemotherapie Chirurgischer Infektionen*, Brückner, W. L. and Pfirmann, R. W. (eds), München-Wien-Baltimore, Urban & Schwarzenberg, p. 3, 1985. Accordingly, whether or not pre-incubation of cells with taurolidine would affect their subsequent response to LPS stimulation was examined. Similar reductions in TF expression were observed when cells were pre-exposed to 100 μg/ml taurolidine for thirty minutes, rinsed, and then exposed to LPS, compared to experiments in which taurolidine and LPS were added concurrently. Thus, direct contact between taurolidine and LPS was not necessary for taurolidine to block the subsequent induction of TF expression by LPS.

Figure 3A:
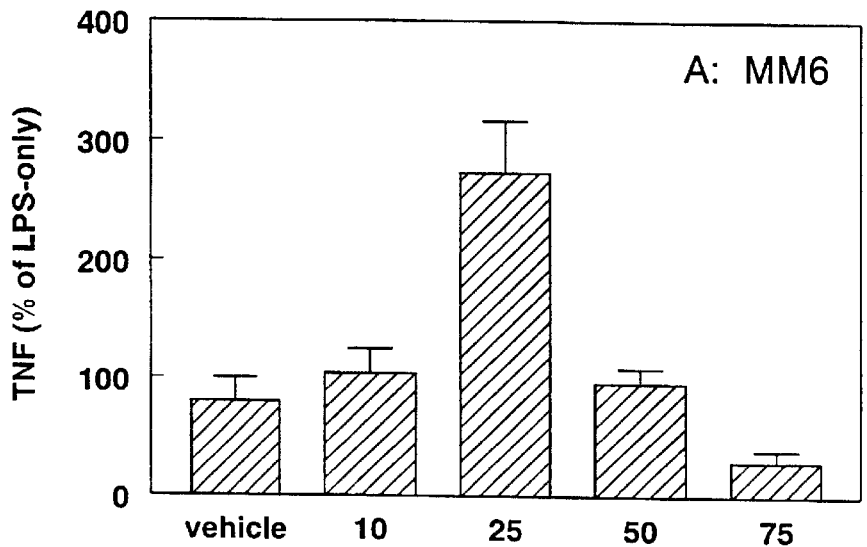
FIG. 3A and FIG. 3B are graphs depicting taurolidine inhibition of LPS-induced alpha tissue necrosis factor (TNFα) expression by monocytic cells as determined by assay procedures.
Figure 3B:
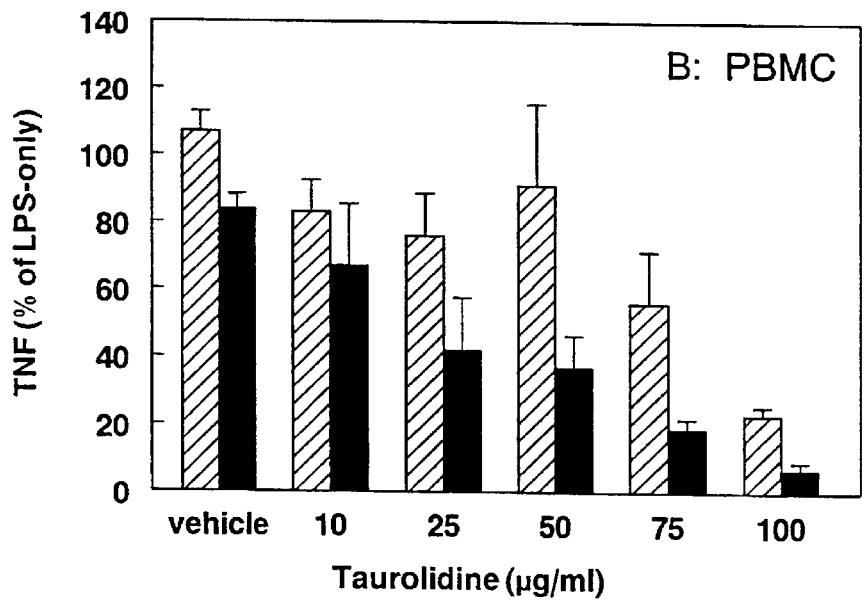

Taurolidine inhibited LPS-induced secretion of TNFα by MM6 cells and PBMC (FIG. 3). MM6 cells were slightly more sensitive to taurolidine, since maximal inhibition was obtained with 75 μg/ml taurolidine, while 100 μg/ml taurolidine was required to maximally inhibit TNFα secretion by PBMC. For MM6 cells, the concentration-dependence of taurolidine inhibition was biphasic, with high concentrations strongly inhibiting TNFα expression and intermediate concentrations (most particularly, 25 μg/ml) markedly stimulating TNFα secretion. Taurine at 44 μg/ml had no effect on TNFα expression by MM6 cells.

Treating peripheral blood monocytes or cultured MM6 cells with taurolidine strongly inhibited the induction of TF in response to LPS. Expression of TF is an important effector function of activated monocytes in sepsis and, in particular, previous studies have shown that blocking antibodies to TF can protect baboons from the lethal effects of intravenous *E. coli* in an animal model of gram-negative septic shock (Taylor, et al., "Lethal *E. coli* septic shock is prevented by blocking tissue factor with monoclonal antibody," *Circ Shock* 33:127 (1991)) and can attenuate the coagulopathy associated with LPS injection into chimpanzees (Levi, et al, "Inhibition of endotoxin-induced activation of coagulation and fibrinolysis by pentoxifylline or by a monoclonal anti-tissue factor antibody in chimpanzees," *J Clin Invest* 93:114 (1994)). Therefore, the ability of taurolidine to block the induction of TF in monocytes is an important aspect of its clinical efficacy in treating sepsis.

In order to determine if taurolidine would inhibit LPS-induced TF expression in PBMC in their native milieu, i.e., whole blood, a tissue factor activity assay was performed. LPS (10 ng/ml) and taurolidine (100–500 μg/ml) or equal dilutions of the taurolidine vehicle were added to 5 ml aliquots of heparinized blood, and the blood was incubated in 50 ml centrifuige tubes at 37° C., rotating on a horizontal rotator at 120 rpm. After 4 hours, PBMC were purified from the blood using Histopaque as described previously. Cells were lysed by 3 freeze-thaw cycles, and used as a source of TF in coagulation assays. For these assays, 50 μl of lysate (at $2 \times 10^7$ cells/ml) was added to 50 μl pooled normal human plasma, incubated for 30 seconds at 37° C., then 50 μl of 25 MM $CaCl_2$ was added and clot formation assayed using a Diagnostica Stago ST4 coagulometer. Protein content of the cell samples was determined by bicinchoninic acid assay (Pierce Chemical Company, Rockford, Ill.), and used to normalize the clotting data. A standard curve was made with descyto TF reconstituted in PS/PC vesicles according to the method of Mimms et al. (Mimms, et al., "Phospholipid vesicle formation and transmembrane protein incorporation using octyl glucoside," *Biochemistry* 20:833–840 (1981)). One unit of TF was defined as that which caused clot formation at 50 seconds of incubation with $CaCl_2$. The TF activity assays were performed on LPS-induced PBMC after 4 hour treatment in whole blood. A dose-response effect of taurolidine on monocyte TF is illustrated in Table II. Taurolidine at 100 μg/ml decreased TF activity by 12%; 200 μg/ml decreased activity by approximately 60%, and treatment with 500 μg/ml taurolidine resulted in loss of approximately 75% of TF activity. Thus, higher concentrations of taurolidine were required to inhibit TF when the PBMC were treated with whole blood when compared to PBMC in culture medium. Further, lower concentrations of taurolidine were required to down-regulate TF expression than were needed to induce apoptosis as described below.

In addition to its role in the pathology of sepsis, TF expression on the surface of leukemia cells (especially acute myelogenous leukemias (AML) and

TABLE II

Effect of Taurolidine Treatment on Coagulation Activity of LPS-induced PBMC

| Treatment | % of control[a] |
|---|---|
| control | 100 |
| vehicle | 123.5 ± 29.0 |
| 100 μg/ml taurolidine | 87.7 ± 6.6 |
| 200 μg/ml taurolidine | 41.7 ± 8.0 |
| 500 μg/ml taurolidine | 26.5 ± 10.6 |

[a]Heparinized blood was incubated in the presence of LPS and varying amounts of taurolidine, then PBMC were purified, and coagulation assays performed on cell lysates. Units of TF per mg protein were calculated as described above, and data expressed as percentage of LPS-only ("control") samples. Data shown are mean ± S.D. of two experiments.

acute lymphoblastic leukemias (ALL) is associated with severe coagulopathies in leukemic patients (Bauer, et al., "Tissue factor gene expression in acute myeloblastic leukemia," *Thromb Res* 56:425–430 (1989); Hair, et al., "Tissue factor expression in human leukemia cells," *Leuk Res* 20:1–11 (1996); and Tanaka, M. and Yamanishi, H., "The expression of tissue factor antigen and activity on the surface of leukemic cells," *Leuk Res* 17:103–111 (1993). These coagulopathies can include life-threatening thrombotic and bleeding episodes, as well as the development of disseminated intravascular coagulation (DIC). Furthermore, episodes of thrombosis and DIC in such leukemic patients can be induced by chemotherapy. Therefore, the ability of taurolidine to reduce expression of TF by leukemic cells (exemplified by the MM6 cell line) should be beneficial in reducing the incidence and severity of coagulopathies in leukemic patients, even at doses which do not kill the leukemia cells.

Effect of Taurolidine on Cell Viability and Growth Rates

Apoptosis is a controlled form of cell death characterized by the fact that neither parent cells nor apoptotic bodies become membrane-permeable. This characteristic distinguishes apoptosis from necrosis wherein cell death involves rupture of cell membranes. Assessment of apoptosis was performed by determining the cell membrane integrity of various cell lines, continued long-term culture of cells after taurolidine treatment to determine growth rate, and membrane permeability after taurolidine treatment. It was found that taurolidine causes apoptosis rather than necrosis of leukemia cells.

In these experiments, integrity of cell membranes following taurolidine treatment was assessed by exclusion of trypan blue and by measuring the release of LDH in MM6, K-562, HL-60, and REH cells. Since BCS contains significant amounts of LDH, these experiments were conducted on cells cultured in AIM-V+0.01% BCS. Four hour treatment of cells was conducted in AIM-V containing 0.01% BCS in order to allow subsequent LDH assay without interference from BCS (which occurs in when normal culture medium, containing 10% BCS, is used). Thus, MM6 cells ($5 \times 10^5$ cells/ml) were treated with taurolidine for four hours in AIM-V+0.01% BCS, after which an aliquot of the cell suspension was removed for measurement of LDH release. A parallel aliquot of cells was lysed by three cycles of freeze/thaw and the quantity of LDH released was taken to be 100%. Remaining cells were rinsed in HBSS and resuspended in growth medium for measurement of growth rates.

Figure 4A:
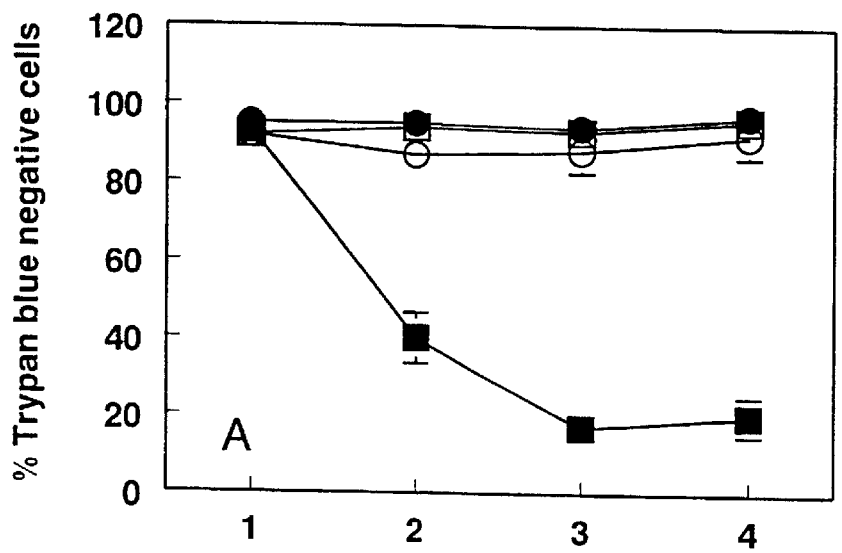
FIG. 4A and FIG. 4B are graphs depicting cell viability and growth rates following taurolidine treatment as determined by assay procedures. MM6 cells were treated with taurolidine as described in FIG. 3. After aliquots were collected for the lactate dehydrogenase (LDH) assay, the remainder of the culture was rinsed in Hank's balanced salt solution (HBSS) and resuspended in RPMI+10% BCS without taurolidine. Counts of trypan blue-negative cells represented in FIG. 4A and total cell number represented in FIG. 4B were recorded daily thereafter (with the measurement at Day 1 being made immediately after the four hour taurolidine treatment). Conditions were no treatment (open squares); 50 µg/ml taurolidine (closed squares); 25 µg/ml taurolidine (open circles); and vehicle alone (closed circles). Cells were subcultured when they reached a concentration of 6×10$^5$ cells/ml. Data are mean±SEM of three experiments.
Figure 4B:
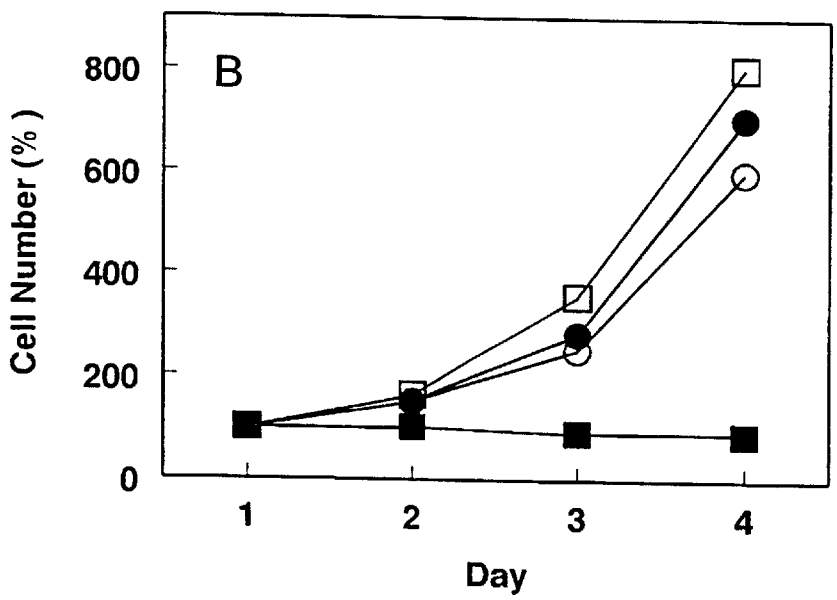
Figure 5A:
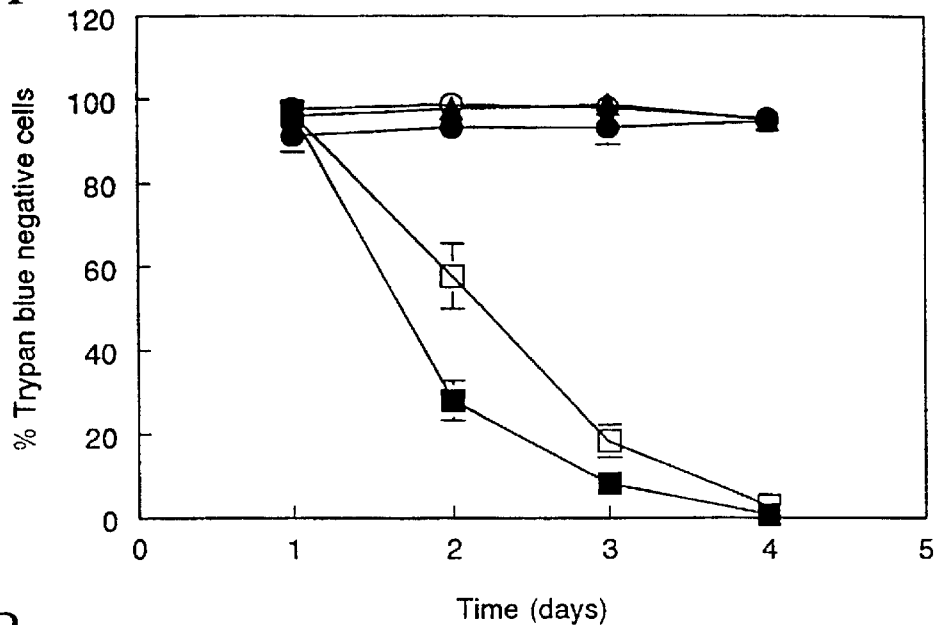
FIGS. 5A and 5B depict cell viability and growth rates for MM6 cell line following taurolidine treatment, in terms of % trypan blue negative cells and % cell number, respectively. Cells were treated with various concentrations of taurolidine for 4 hours in AIM-V+0.01% BCS. After aliquots were collected for LDH assay, the remainder of the culture was rinsed in HBSS and resuspended in RPMI+10% BCS without taurolidine. Counts of trypan blue-negative cells (FIG. 5A), and total cell number (FIG. 5B), were recorded daily thereafter (with the measurement at Day 1 being made immediately after the 4 hour taurolidine treatment). Conditions were: no treatment (open circles); 25 µg/ml taurolidine (closed circles); 50 µg/ml taurolidine (open squares); 100 µg/ml taurolidine (closed squares); and vehicle alone (closed triangles). Doubling times were determined under each condition, and expressed as a percentage of the rate of doubling of untreated cells. These values are located to the right of the growth curves in (FIG. 5B). Cells were subcultured when they reached a concentration of 6×10$^5$ cells/ml. Data are mean±SEM of three experiments.
Figure 5B:
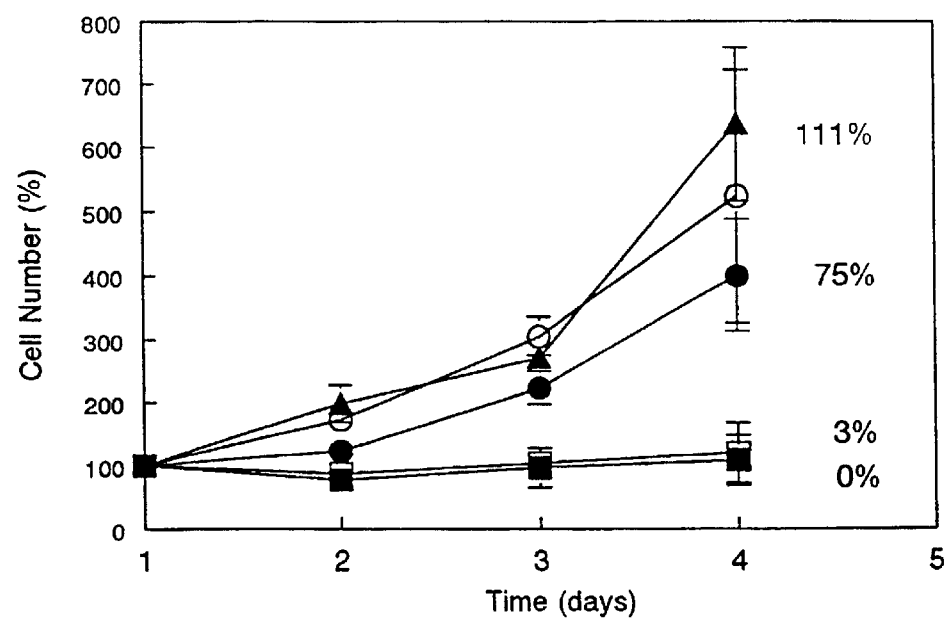
Figure 6A:
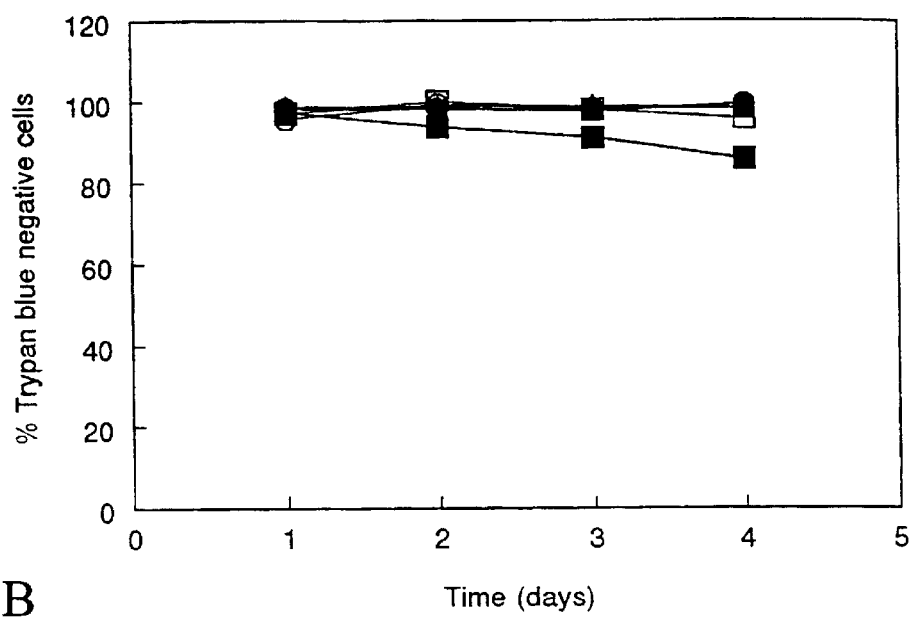
FIGS. 6A and 6B depict cell viability and growth rates for K562 cell line following taurolidine treatment, in terms of % trypan blue negative cells and % cell number, respectively. Cells were treated with various concentrations of taurolidine for 4 hours in AIM-V+0.01% BCS. After aliquots were collected for LDH assay, the remainder of the culture was rinsed in HBSS and resuspended in RPMI+10% BCS without taurolidine. Counts of trypan blue-negative cells (FIG. 6A), and total cell number (FIG. 6B), were recorded daily thereafter (with the measurement at Day 1 being made immediately after the 4 hour taurolidine treatment). Conditions were: no treatment (open circles); 25 µg/ml taurolidine (closed circles); 50 µg/ml taurolidine (open squares); 100 µg/ml taurolidine (closed squares); and vehicle alone (closed triangles). Doubling times were determined under each condition, and expressed as a percentage of the rate of doubling of untreated cells. These values are located to the right of the growth curves in (FIG. 6B). Cells were subcultured when they reached a concentration of 6×10$^5$ cells/ml. Data are mean±SEM of three experiments.
Figure 6B:
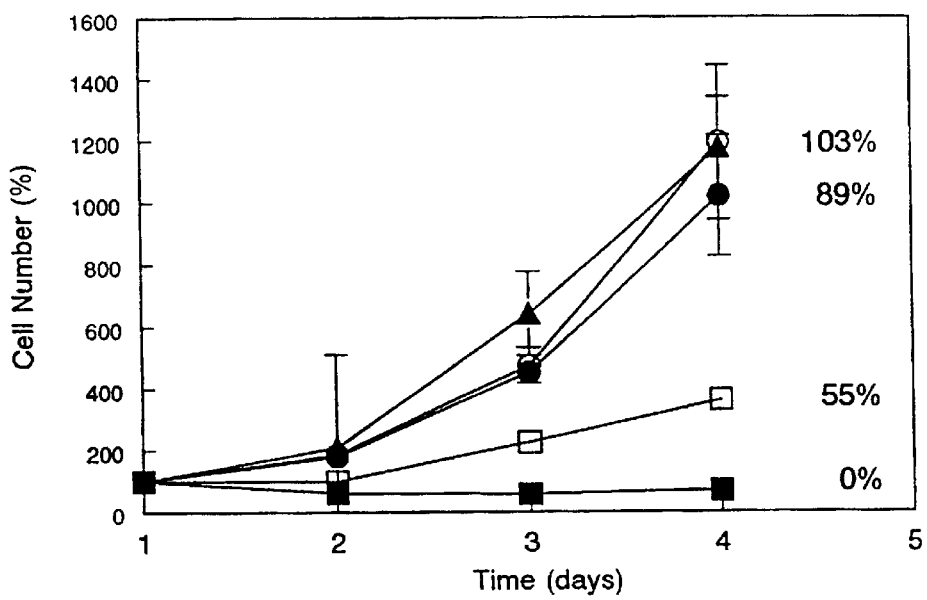
Figure 7A:
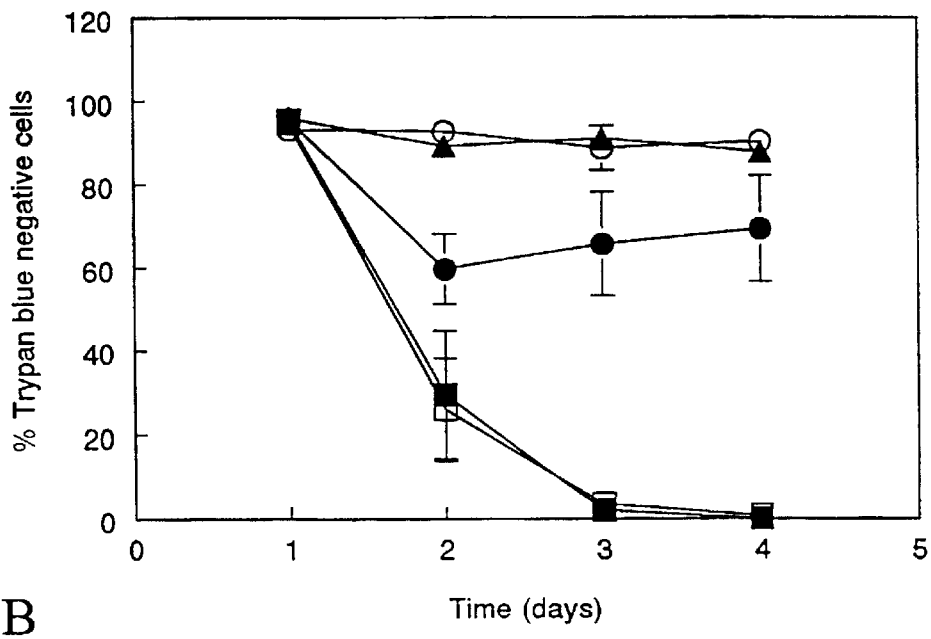
FIGS. 7A and 7B depict cell viability and growth rates for HL-60 cell line following taurolidine treatment, in terms of % trypan blue negative cells and % cell number, respectively. Cells were treated with various concentrations of taurolidine for 4 hours in AIM-V+0.01% BCS. After aliquots were collected for LDH assay, the remainder of the culture was rinsed in HBSS and resuspended in RPMI+10% BCS without taurolidine. Counts of trypan blue-negative cells (FIG. 7A), and total cell number (FIG. 7B), were recorded daily thereafter (with the measurement at Day 1 being made immediately after the 4 hour taurolidine treatment). Conditions were: no treatment (open circles); 25 µg/ml taurolidine (closed circles); 50 µg/ml taurolidine (open squares); 100 µg/ml taurolidine (closed squares); and vehicle alone (closed triangles). Doubling times were determined under each condition, and expressed as a percentage of the rate of doubling of untreated cells. These values are located to the right of the growth curves in (FIG. 7B). Cells were subcultured when they reached a concentration of 6×10$^5$ cells/ml. Data are mean±SEM of three experiments.
Figure 7B:
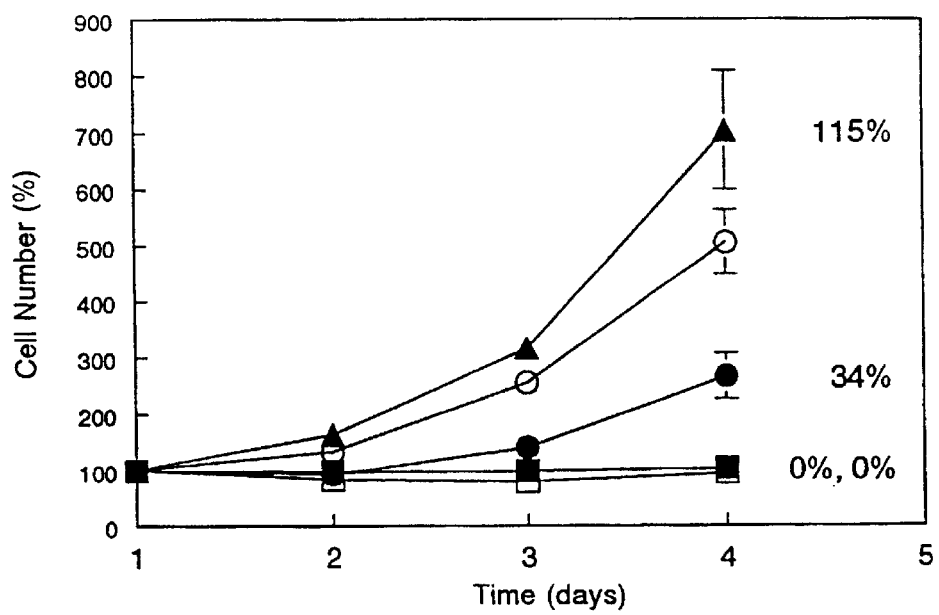
Figure 8A:
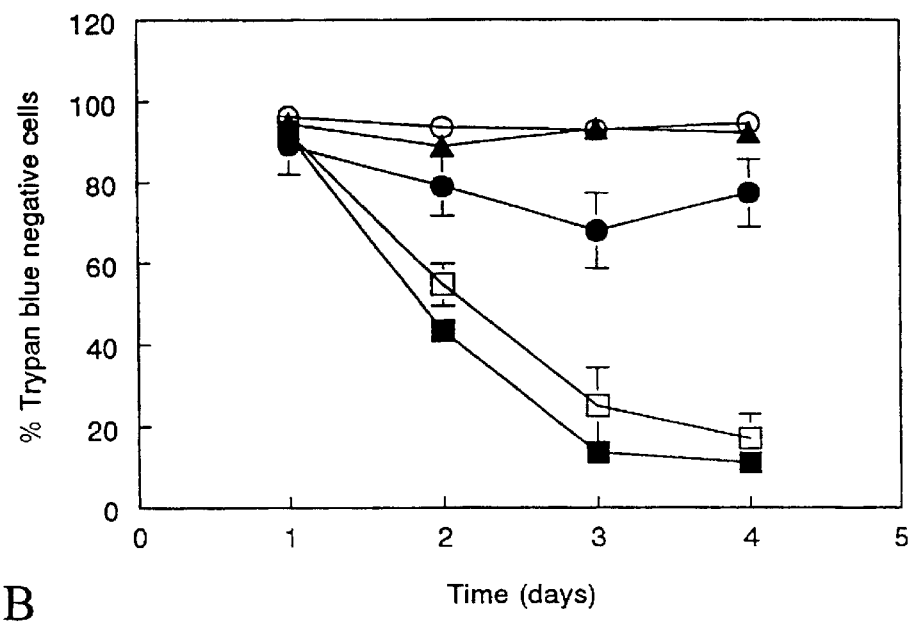
FIGS. 8A and 8B depict cell viability and growth rates for REH cell line following taurolidine treatment, in terms of % trypan blue negative cells and % cell number, respectively. Cells were treated with various concentrations of taurolidine for 4 hours in AIM-V+0.01% BCS. After aliquots were collected for LDH assay, the remainder of the culture was rinsed in HBSS and resuspended in RPMI+10% BCS without taurolidine. Counts of trypan blue-negative cells (FIG. 8A), and total cell number (FIG. 8B), were recorded daily thereafter (with the measurement at Day 1 being made immediately after the 4 hour taurolidine treatment). Conditions were: no treatment (open circles); 25 µg/ml taurolidine (closed circles); 50 µg/ml taurolidine (open squares); 100 µg/ml taurolidine (closed squares); and vehicle alone (closed triangles). Doubling times were determined under each condition, and expressed as a percentage of the rate of doubling of untreated cells. These values are located to the right of the growth curves in (FIG. 8B). Cells were subcultured when they reached a concentration of 6×10$^5$ cells/ml. Data are mean±SEM of three experiments.
Figure 8B:
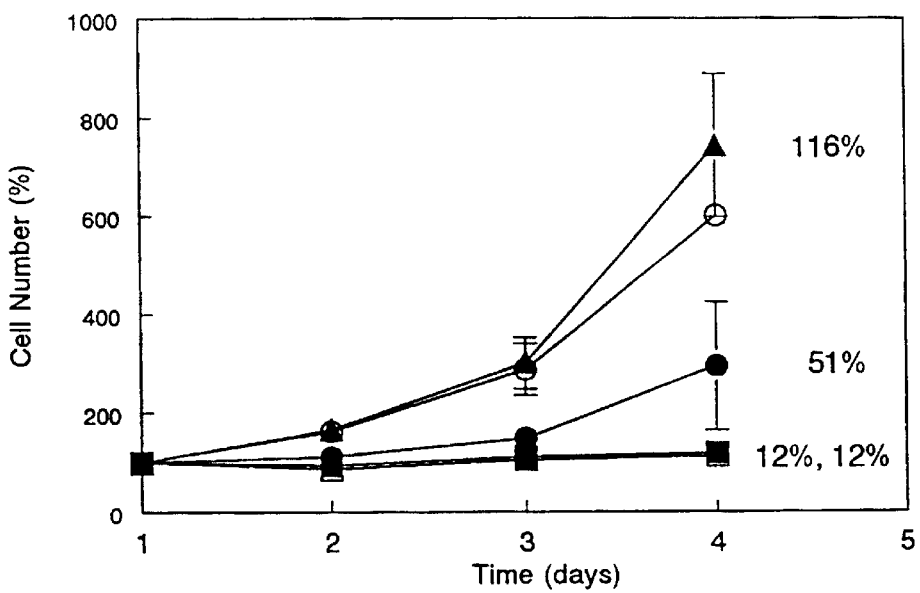
Figure 9A:
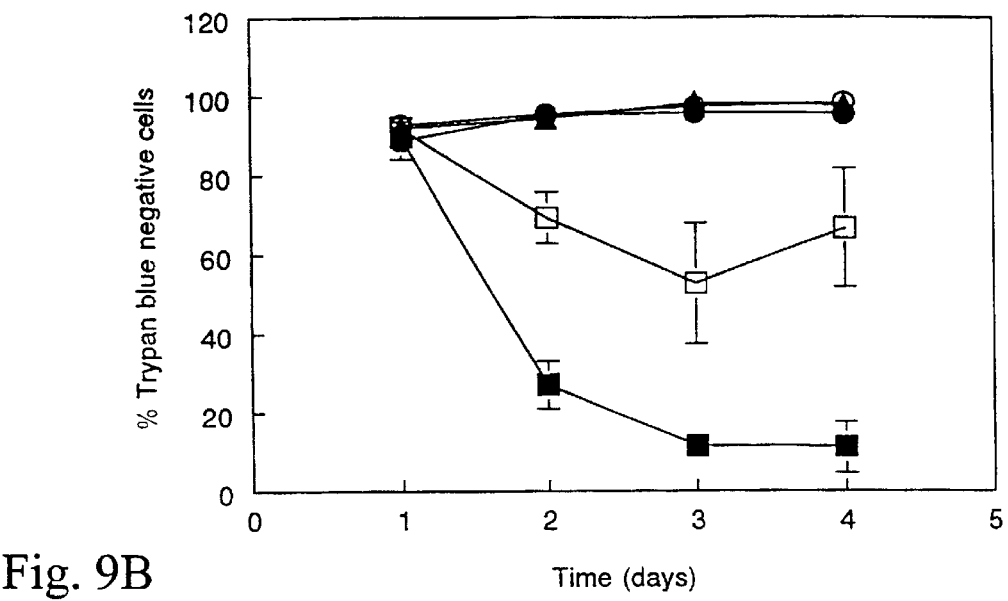
FIGS. 9A and 9B depict cell viability and growth rates for Jurkat cell line following taurolidine treatment, in terms of % trypan blue negative cells and % cell number, respectively. Cells were treated with various concentrations of taurolidine for 4 hours in AIM-V+0.01% BCS. After aliquots were collected for LDH assay, the remainder of the culture was rinsed in HBSS and resuspended in RPMI+10% BCS without taurolidine. Counts of trypan blue-negative cells (FIG. 9A), and total cell number (FIG. 9B), were recorded daily thereafter (with the measurement at Day 1 being made immediately after the 4 hour taurolidine treatment). Conditions were: no treatment (open circles); 25 µg/ml taurolidine (closed circles); 50 µg/ml taurolidine (open squares); 100 µg/ml taurolidine (closed squares); and vehicle alone (closed triangles). Doubling times were determined under each condition, and expressed as a percentage of the rate of doubling of untreated cells. These values are located to the right of the growth curves in (FIG. 9B). Cells were subcultured when they reached a concentration of 6×10$^5$ cells/ml. Data are mean±SEM of three experiments.
Figure 9B:
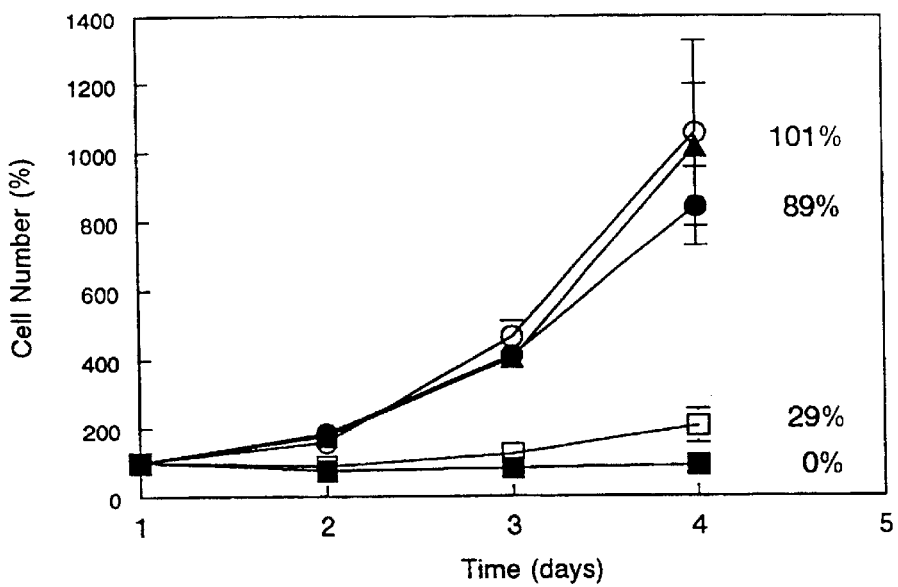

Upon microscopic examination of MM6 cultures treated for four hours with 100 μg/ml taurolidine, the cells appeared to be smaller than control cells and the cultures were observed to contain numerous small, spherical bodies which excluded trypan blue. In one study, the integrity of the cell membrane was assessed by measurement of LDH release in PBMC and MM6 cells cultured in AIM-V+0.01% BCS. After treatment with 0 to 50 μg/ml taurolidine for four hours, LDH levels in the treated cultures ranged from 6 to 9% of that of freeze/thaw lysed cells (mean values of three separate experiments), which was not significantly different from LDH levels in cultures not treated with taurolidine. Additionally, after four hour treatment, control and taurolidine-treated cells were equally able to exclude trypan blue (FIG. 4A, Day 1). However, when taurolidine-treated MM6 cells were rinsed and resuspended in growth medium, 65% of cells exposed to 50 μg/ml taurolidine became trypan blue-positive on the day following treatment (FIG. 4A, Day 2), indicating that the plasma membrane had become permeable. In contrast, only 5% of untreated ("control") and vehicle-treated cells were trypan blue-positive. Cells treated with 50 μg/ml taurolidine for four hours failed to grow when returned to growth medium, while cells treated with vehicle alone or with 25 μg/ml taurolidine exhibited growth rates similar to that observed with untreated cells (FIG. 4B). In another study, K-562, HL-60, and REH cells were tested after a four hour treatment with taurolidine, and the results are summarized in Table III.

HL-60 cells treated with 50 μl taurolidine. In these samples, LDH present in the culture medium was 8.3±2.3% of that released by completely lysed cells, compared with 2.3±0.8% measured in control cultures. All samples from all other cell lines displayed LDH levels which were ≦7% of lysed cell samples (n=3). After 4 hour treatment, cells were rinsed and returned to growth medium and monitored for viability and growth over the following 3 days. Concentrations of taurolidine from 25 μg/ml to 100 μ/ml were used in order to highlight differences in sensitivity of cell lines to taurolidine. Trypan blue assay of all samples were equivalent to control on Day 1 (after 4 hours of treatment) indicating that taurolidine treatment did not cause rapid permeability of cell membranes, suggesting that this compound did not cause cellular necrosis. However, over the following days, all leukemia-derived-cell lines demonstrated progressive

TABLE III

Results from a Four Hour Treatment with Taurolidine

| Cell Type | Conc. Taurolidine | LDH (% of total)[a] | growth rate (% of control)[b] |
|---|---|---|---|
| K-562 (chronic myeologenous leukemia) | control | 8 | 100 |
| | 50 μg/ml | 6 | 52 |
| | 100 μg/ml | 8 | 0 |
| | vehicle | 6 | 80 |
| HL-60 (acute myeloid leukemia) | control | 5 | 100 |
| | 50 μg/ml | 5 | 0 |
| | 100 μg/ml | 6 | 3 |
| | vehicle | 4 | 92 |
| REH (acute lymphocytic leukemia) | control | 4 | 100 |
| | 50 μg/ml | 6 | 1 |
| | 100 μg/ml | 5 | 18 |
| | vehicle | 5 | 119 |

[a]LDH was measured immediately after four hour taurolidine treatment.
[b]Growth rate was measured over three days following treatment.

permeability to trypan blue after treatment with concentrations of taurolidine of 50 μg/ml or greater, with the exception of K562 cells (FIGS. 5A, 6A, 7A, 8A, and 9A). MM6, K562, and Jurkat cells did not show an increase in trypan blue staining after treatment with 25 μg/ml taurolidine, while HL-60 and REH cells were more sensitive. As explained, eventual permeability of cell membranes is inevitable in in vitro apoptosis. K562 cells demonstrated an inhibition of growth after taurolidine treatment of 50 μg/ml or greater as did the other leukemia-derived cell lines (FIGS. 5B, 6B, 7B, 8B, and 9B). Cell lines demonstrated differing sensitivities to taurolidine in regard to cell growth, with K562 and Jurkat cells being least affected, and HL-60 growth being most inhibited after taurolidine treatment.

Figure 10A:
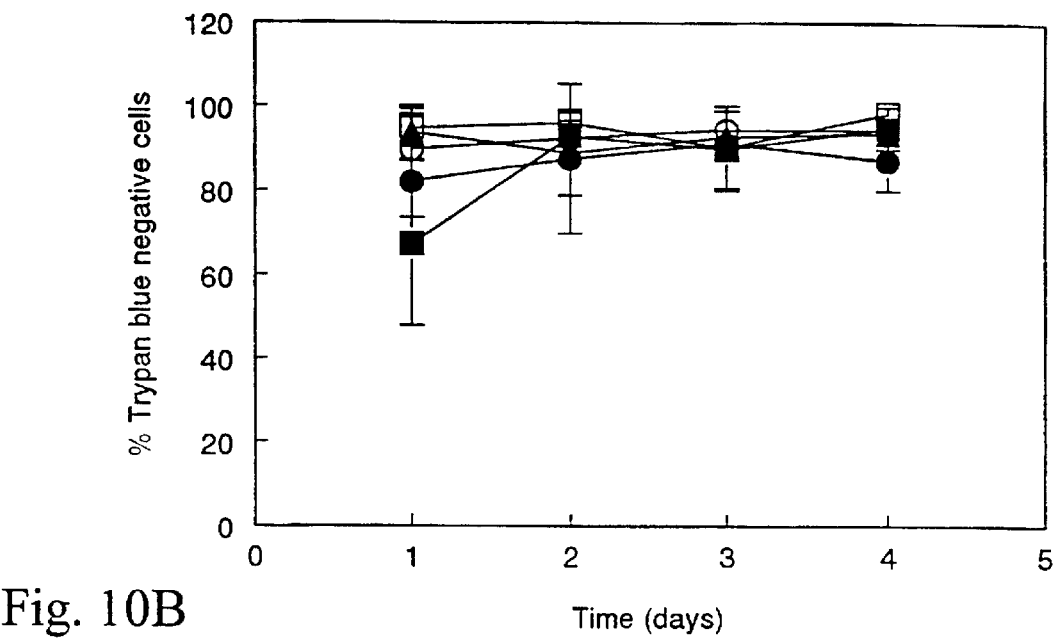
FIGS. 10A and 10B depict cell viability and growth rates for ECV304 cell line following taurolidine treatment, in terms of % trypan blue negative cells and % cell number, respectively. Cells were treated with various concentrations of taurolidine for 4 hours in AIM-V+0.01% BCS. After aliquots were collected for LDH assay, the remainder of the culture was rinsed in HBSS and resuspended in RPMI+10% BCS without taurolidine. Counts of trypan blue-negative cells (FIG. 10A), and total cell number (FIG. 10B), were recorded daily thereafter (with the measurement at Day 1 being made immediately after the 4 hour taurolidine treatment). Conditions were: no treatment (open circles); 25 µg/ml taurolidine (closed circles); 50 µg/ml taurolidine (open squares); 100 µg/ml taurolidine (closed squares); and vehicle alone (closed triangles). Doubling times were determined under each condition, and expressed as a percentage of the rate of doubling of untreated cells. These values are located to the right of the growth curves in (FIG. 10B). Cells were subcultured when they reached a concentration of $6 \times 10^5$ cells/ml. Data are mean±SEM of three experiments.
Figure 10B:
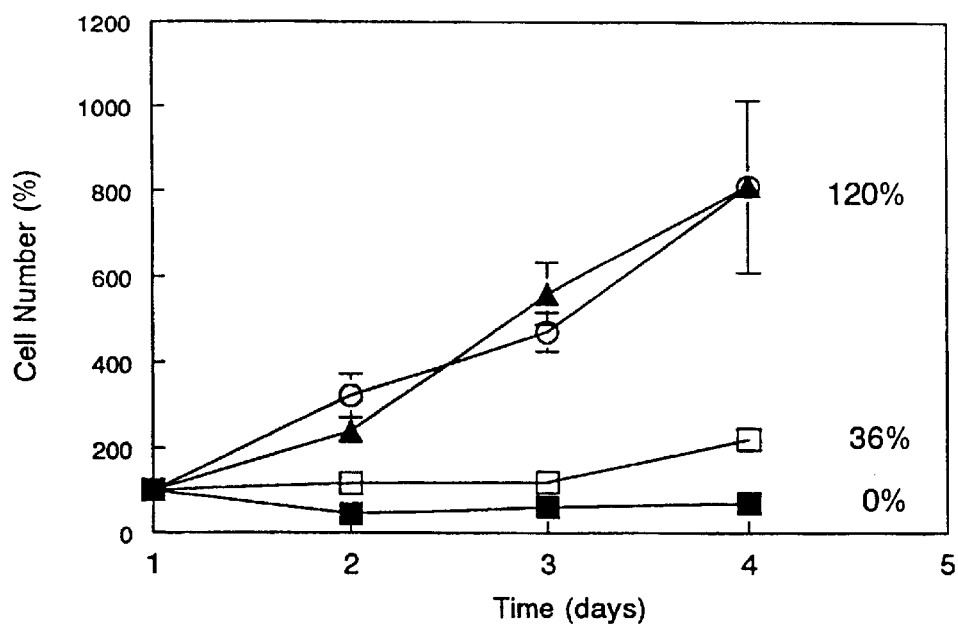
Figure 11A:
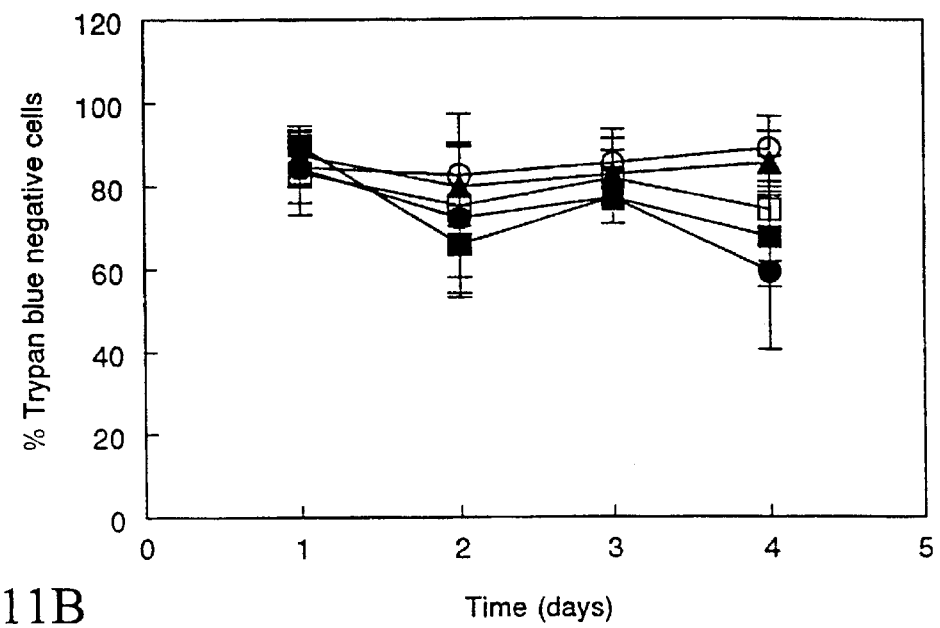
FIGS. 11A and 11B depict cell viability and growth rates for GM5387 cell line following taurolidine treatment, in terms of % trypan blue negative cells and % cell number, respectively. Cells were treated with various concentrations of taurolidine for 4 hours in AIM-V+0.01% BCS. After aliquots were collected for LDH assay, the remainder of the culture was rinsed in HBSS and resuspended in RPMI+10% BCS without taurolidine. Counts of trypan blue-negative cells (FIG. 11A), and total cell number (FIG. 11B), were recorded daily thereafter (with the measurement at Day 1 being made immediately after the 4 hour taurolidine treatment). Conditions were: no treatment (open circles); 25 µg/ml taurolidine (closed circles); 50 µg/ml taurolidine (open squares); 100 µg/ml taurolidine (closed squares); and vehicle alone (closed triangles). Doubling times were determined under each condition, and expressed as a percentage of the rate of doubling of untreated cells. These values are located to the right of the growth curves in (FIG. 11B). Cells were subcultured when they reached a concentration of $6 \times 10^5$ cells/ml. Data are mean±SEM of three experiments.
Figure 11B:
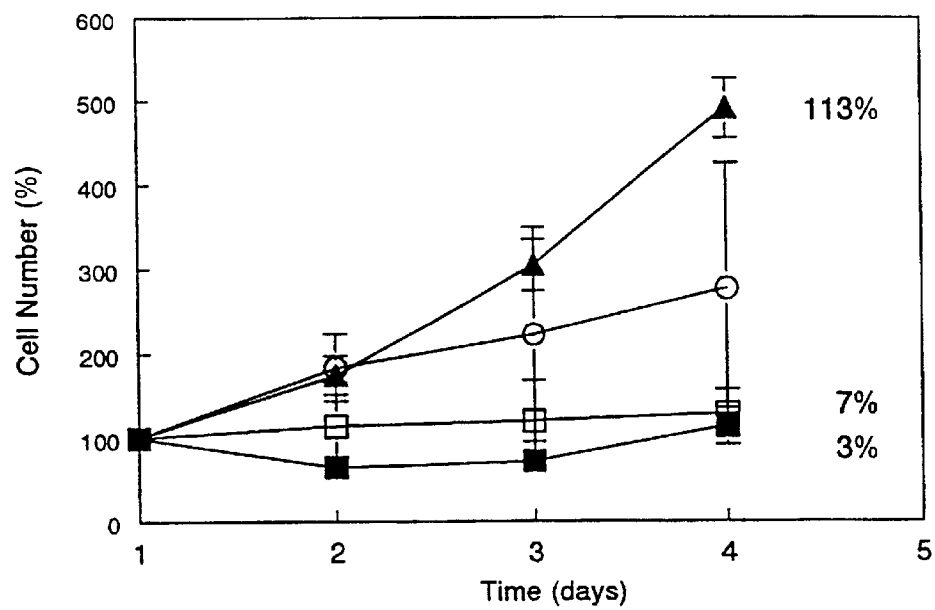
Figure 12A:
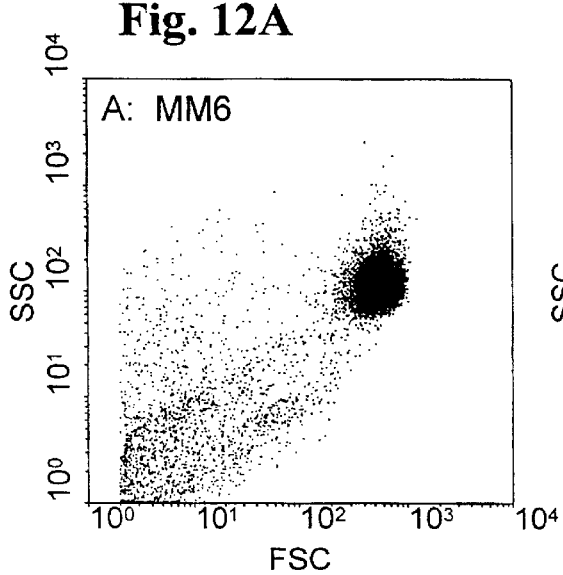
FIG. 12A, FIG. 12B, FIG. 12C, and FIG. 12D are flow cytometric analyses depicting changes in cell morphology following taurolidine treatment. MM6 and PBMC were treated for three hours with taurolidine, and then treated and untreated control cells were processed for flow cytometry. Monocytes in PBMC samples were identified by staining with FITC-conjugated anti-CD14, and lymphocytes by FITC-conjugated anti-CD3 and PE-conjugated anti-CD19.
Figure 12B:
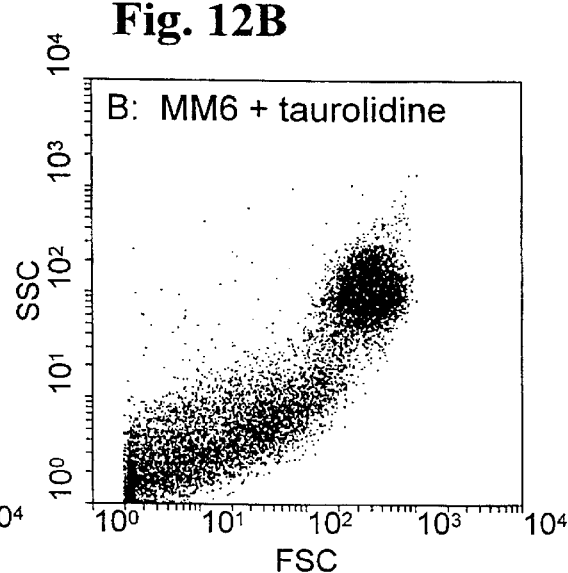
Figure 12C:
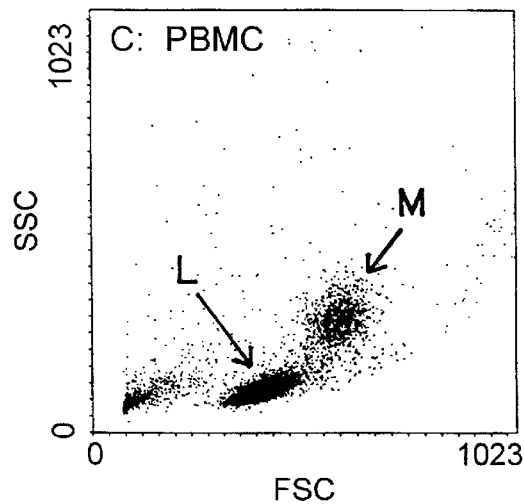
Figure 12D:
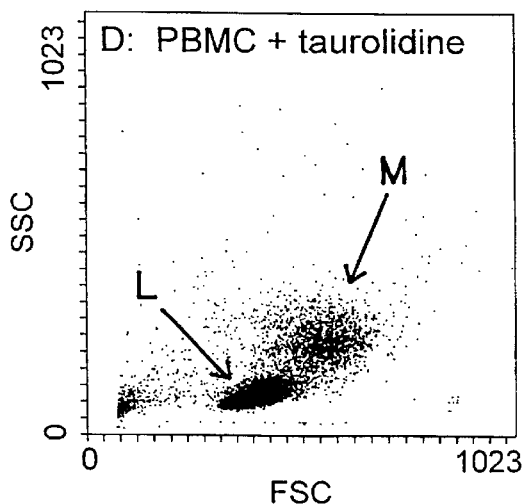

The adherent cell lines ECV304 (endothelial cells) and GM5387 (fibroblasts) did not demonstrate a significant increase in trypan blue staining of cells during 4 day growth after taurolidine treatment (FIGS. 10A and 11A). However, proliferation of these cells was inhibited after treatment with 50 and 100 μg/ml taurolidine (FIGS. 10B and 11B).

Detection of Apoptosis

The effect of taurolidine on cell lines of various lineages with respect to apoptosis was evaluated. Treatment with effective amounts of taurolidine resulted in apoptosis in a variety of monocytic, granulocytic and numerous leukemic cell lines, but not in lymphocytes.

Following treatment with either taurolidine or the vehicle solution, cell death was assessed in one of two ways. In the first method, the DNA fragmentation pattern characteristic of apoptosis was detected by extracting low molecular weight DNA from cells using a phosphate-citrate buffer (Darzynkiewicz, et al., "Assays of cell viability: discrimination of cells dying by apoptosis," *Methods Cell Biol* 41:15 (1994)) and subjecting the extracted DNA to agarose gel electrophoresis.

In the second method, DNA fragmentation was detected via TUNEL assay according to the manufacturer's instructions. With this methodology, 2×10$^6$ cells were fixed with 2% paraformaldehyde, permeabilized with 0.1% Triton X-100/0.1% citrate, incubated at 37° C. with terminal deoxynucleotidyl transferase and FITC-dUTP, rinsed and analyzed by flow cytometry. Enhanced FITC signal indicates apoptosis-specific DNA fragmentation. Gavriali, et al, "Identification of programmed cell death in situ via specific labeling of nuclear DNA fragmentation," *J Cell Biol* 119:493 (1992). Parallel aliquots of unfixed cells were treated with PI and FITC-conjugated anti-CD14 and analyzed by flow cytometry, in order to identify cells with permeable cell membranes (since PI binds to DNA but is excluded from cells with intact plasma membranes) and also to determine the cell-specificity of the apoptotic signal.

A Becton-Dickinson FACSCalibur instrument was used for flow cytometric analysis of cells. Assessment of cell diameter (forward scatter; FCS) and granularity (side scatter; SSC).was carried out on unfixed cells. Discrimination between lymphocytes and monocytes was made possible by their characteristic differences in FSC and SSC, and confirmed by staining monocytes with FITC-labeled anti-CD14 antibodies and lymphocytes with a combination of FITC-conjugated anti-CD3 and PE-conjugated anti-CD19. After incubation with taurolidine (with or without concomitant LPS treatment), cells were rinsed twice in phosphate-buffered saline containing 0.1% bovine serum albumin (PBSA) and 1×10$^6$ cells were resuspended in 0.1 ml PBSA. After 5 μl FITC-conjugated anti-CD14 was added, cells were incubated in the dark on ice for 15 minutes and then centrifuged at 250×g. Cells were resuspended in 500 μl PBSA containing 5 μg/ml PI and subjected to flow cytometry.

Taurolidine-treated MM6 cells and peripheral blood monocytes displayed reduced cell size as illustrated by a decrease in FSC and SSC when cells were analyzed by flow cytometry (FIG. 12). After a three hour treatment with taurolidine, MM6 cells demonstrated an approximately 30% decrease in FSC, as did peripheral blood monocytes after a six hour treatment. These morphological changes (reduced cell size and appearance of spherical bodies) were concomitant with an intact plasma membrane, indicating that taurolidine induces apoptosis in monocytic cells.

Figure 13:
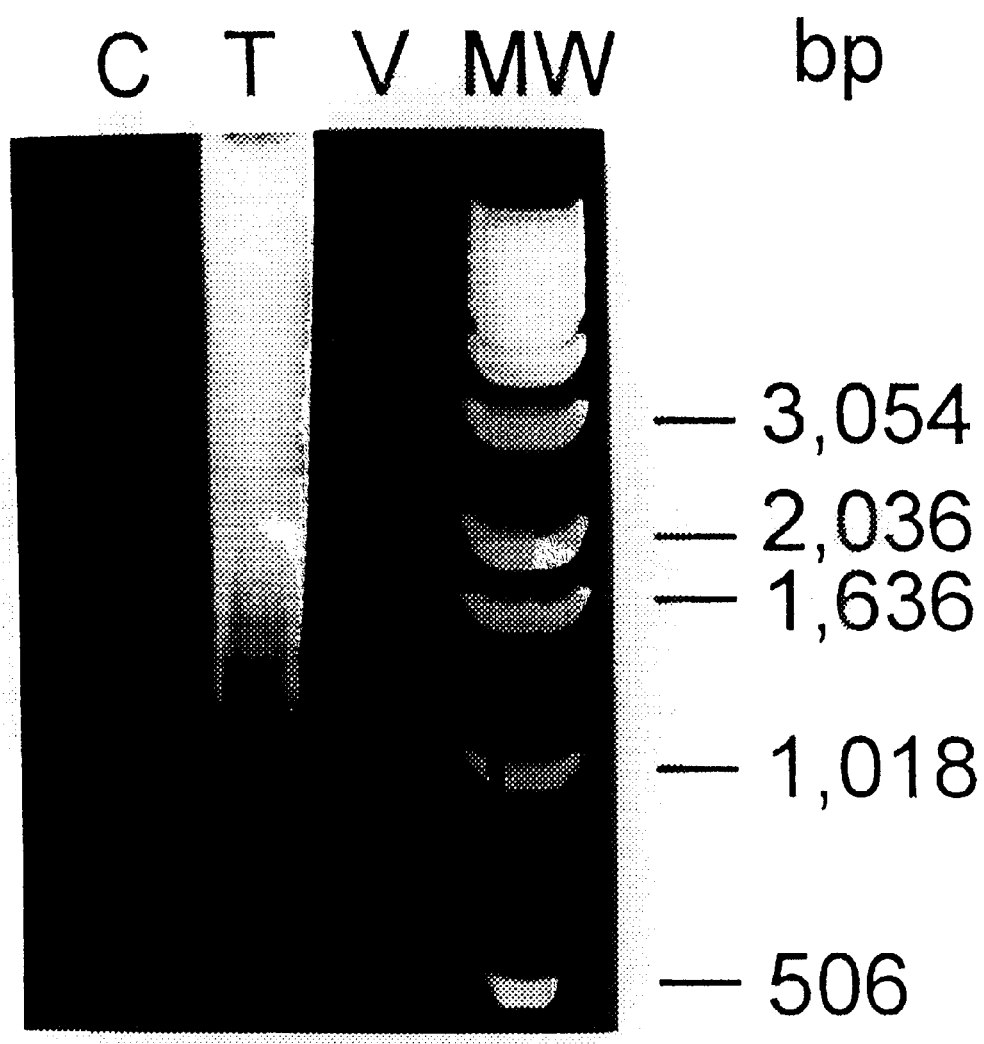
FIG. 13 is an agarose gel depicting DNA fragmentation in response to taurolidine treatment as determined by assay procedures. MM6 cells were incubated with taurolidine or vehicle in RPMI+10% BCS for four hours. Cells were harvested and low molecular weight DNA extracted as described below. C=control cells without taurolidine or vehicle treatment; T=treated with 50 µg/ml taurolidine; V=treated with vehicle alone; and MW=molecular weight markers.

Apoptosis is associated with fragmentation of genomic DNA in the internucleosomal linker regions, which can be visualized as a characteristic ladder of DNA fragments upon gel electrophoresis. Arends, M. J. and Wyllie, A. H., "Apoptosis: mechanisms and roles in pathology," *Int Rev Exp Path* 32:223 (1991). Accordingly, low molecular weight DNA was extracted from taurolidine-treated MM6 cells and subjected to electrophoresis in agarose gels. Cells treated with 50 lμg/ml taurolidine for four hours exhibited a prominent ladder pattern of DNA fragments, while untreated and vehicle-treated cells did not (FIG. 13). These cells had not been treated with LPS; however, identical results were seen when LPS was present during taurolidine treatment. These results support the conclusion that taurolidine induces apoptosis in MM6 cells.

In order to examine if taurolidine treatment induced apoptosis in peripheral blood monocytes, a technique was employed for evaluating DNA fragmentation that could be applied to mixed populations of monocytes and lymphocytes. Consequently, TUNEL analysis was performed on PBMC at 3, 6, or 24 hours after treatment with 25 to 100

μg/ml taurolidine. Aliquots of harvested cells were also labeled with FITC-conjugated anti-CD14 antibodies and PI, which allowed identification of monocytes (CD14-positive cells) and cells with damaged cell membranes (PI-positive cells). While relatively few of the PBMC were TUNEL-positive after a three hour incubation, a substantial population of TUNEL-positive cells was readily apparent after six hours of incubation with 100 μg/ml taurolidine (events to the right of the vertical line in FIG. 14), concomitant with a large loss of TUNEL-negative monocytes (region R1 in FIG. 14; see also Table IV). Thus, nearly 75% of the monocytes were TUNEL-positive following treatment with 100 μg/ml taurolidine for six hours. Confirmation that the TUNEL-positive cells were monocytes was obtained by staining with FITC-conjugated anti-CD14. Lower doses of taurolidine (25 and 50 μg/ml) resulted in lower levels of induction of apoptosis (Table IV). Taurolidine-treated and control cells exhibited equivalently low levels of PI-positive cells at six hours, indicating that the cell membranes remained intact at this time (Table IV). In another study summarized in Table V, taurolidine-treated polymorphonuclear cells (granulocytes) at 100 μg/ml, MM6 cells (monocytic leukemia cell line) at 50 μg/ml, and acute myeloid leukemia cell line (HL-60) at 50 μg/ml exhibited a high level of apoptosis as indicated by the low percentage of % TUNEL-negative cells, and the low percentage of propidium iodide positive cells confirmed that the treated cells remained intact.

In contrast to its effect on monocytes, treatment with up to 100 μg/ml taurolidine for six hours did not induce detectable apoptosis in the lymphocyte

TABLE IV

Dose-Response of PBMC to Taurolidine: 6 Hour Treatment[a]

| Cell Type | Treatment | % Propidium Iodide Positive | % TUNEL-Negative[b] |
|---|---|---|---|
| All Cells | Control | 11.0 ± 1.6 | |
| | 25 μg/ml taurolidine | 9.0 ± 3.2 | |
| | 50 μg/ml taurolidine | 12.2 ± 5.6 | |
| | 100 μg/ml taurolidine | 9.0 ± 3.5 | |
| Monocytes | Control | | 100 |
| | 25 μg/ml taurolidine | | 88.3 ± 2.7 |
| | 50 μg/ml taurolidine | | 67.8 ± 18.0 |
| | 100 μg/ml taurolidine | | 25.1 ± 11.8 |
| Lymphocytes | Control | | 100 |
| | 25 μg/ml taurolidine | | 100.2 ± 7.0 |
| | 50 μg/ml taurolidine | | 99.8 ± 3.4 |
| | 100 μg/ml taurolidine | | 101.9 ± 3.1 |

Figure 14A:
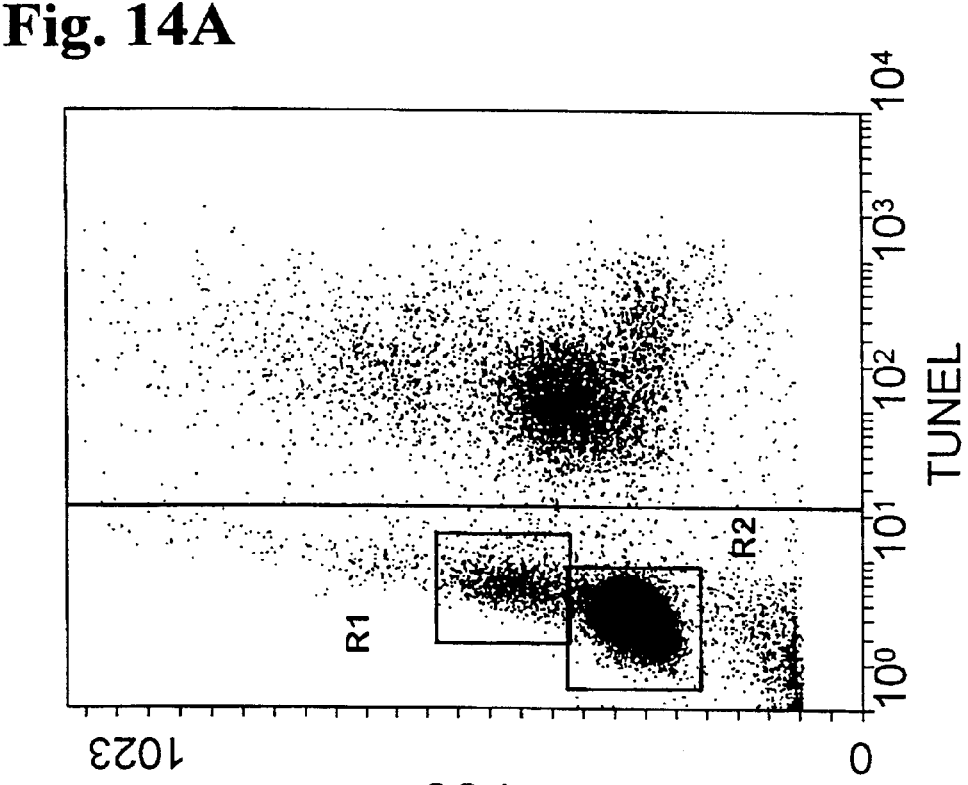
FIG. 14A and FIG. 14B are terminal deoxytransferase-mediated deoxyuridine-triphosphate-biotin nick end labeling assay (TUNEL) analyses of control cells and taurolidine-treated PBMC, respectively. Cells were incubated with 100 µg/ml taurolidine for six hours and processed for TUNEL analysis as given below. Parallel samples were stained with FITC-conjugated anti-CD14 and propidium iodide (PI) as described below. Ten thousand events were recorded per sample. TUNEL signal (x-axis) is a measure of DNA fragmentation, which FSC (y-axis) is related to cell size. TUNEL-negative lymphocytes are bounded by the rectangle R1, while TUNEL-negative monocytes (CD14 positive cells) are bounded by the rectangle R2. The vertical line indicates demarcation between TUNEL-negative and TUNEL-positive cells. There were minimal numbers of PI-positive cells in the six hour samples (see Table IV).
Figure 14B:
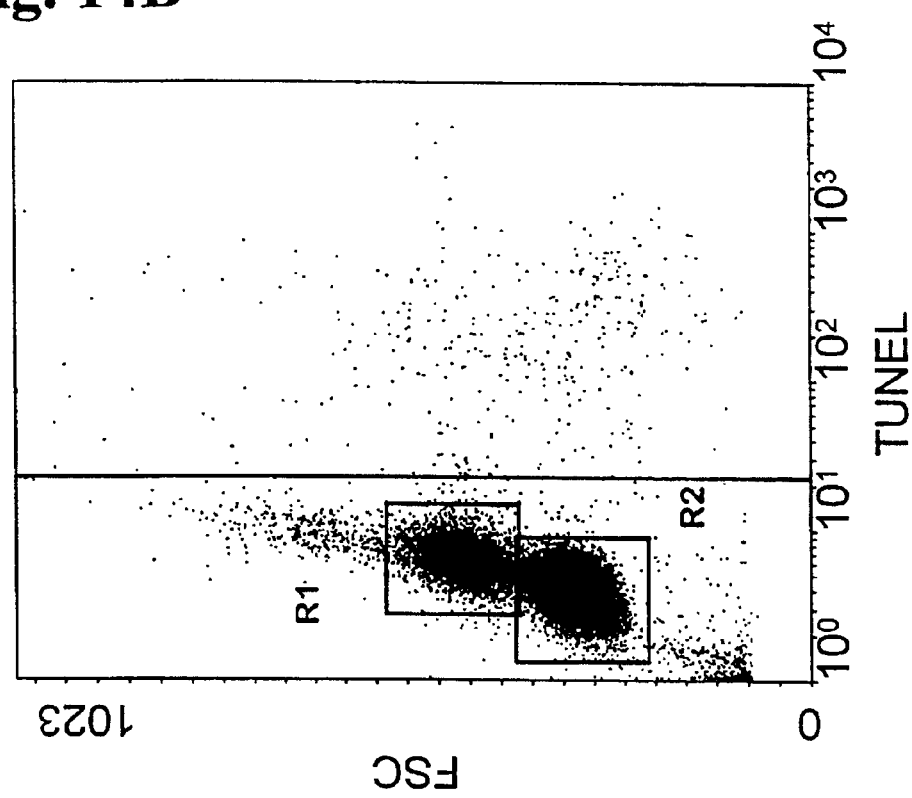

[a]Analysis by flow cytometry after staining cells with FITC-conjugated anti-CD14 and PI, and processing for TUNEL. Data are mean ± SD of two experiments.
[b]Percent of cells present in the TUNEL-negative region in control samples.

population of PBMC, with essentially 100% of the cells remaining TUNEL-negative (FIG. 14 and Table IV).

Taurolidine at 100 μg/ml induced apoptosis of approximately 75% of purified peripheral blood monocytes when these cells were incubated in culture medium. However, in order to more closely mimic the milieu of leukocytes in vivo, induction of apoptosis in PBMC by taurolidine was studied in whole blood (anticoagulated with heparin). As before, apoptosis was quantitated by measuring the loss of monocytes from a TUTNEL-negative (no DNA fragmentation), CD 14 positive population of cells which was concomitant with the appearance of a TUNEL-positive population of cells. Treatment of PBMC in whole blood resulted

TABLE V

Induction of Apoptosis by Taurolidine

| Cell Type | Conc. Taurolidine | Length of Incubation | % Propidium Iodide Positive Cells[a] | % TUNEL-Negative Cells[b] |
|---|---|---|---|---|
| granulocytes[c] | control | 6 hours | 1 | 98 |
| | 100 μg/ml | 6 hours | 2 | 8 |
| Mono Mac 6[d] | control | 3 hours | 10 | 98 |
| | 50 μg/ml | 3 hours | 7 | 44 |
| HL-60[e] | control | 3 hours | 7 | 85 |
| | 50 μg/ml | 3 hours | 5 | 35 |

Figure 15A:
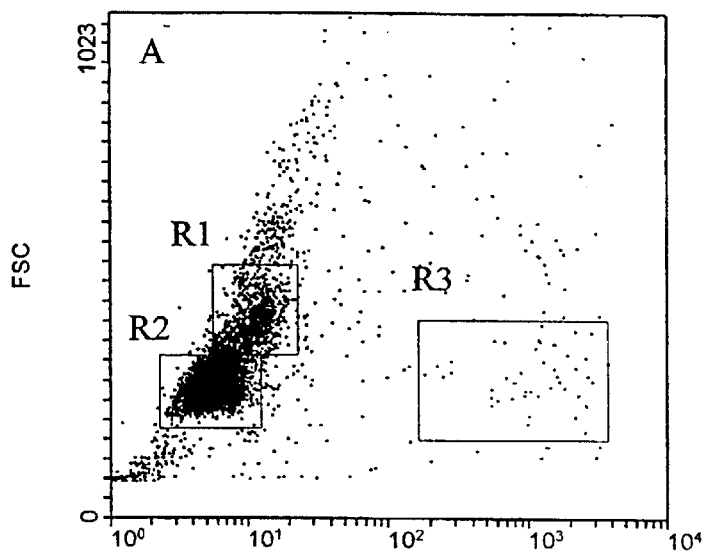
FIGS. 15A, 15B, and 15C depict TUNEL analysis of PBMC treated with taurolidine in whole blood, for control cells, taurolidine-treated cells, and anisomycin-treated cells, respectively. Cells were incubated with 500 µg/ml taurolidine for 4 hours, resuspended in fresh medium, incubated for two hours further and processed for TUNEL analysis. Parallel samples were stained with FITC-conjugated anti-CD14 and PI as described herein. Ten thousand events were recorded per sample. TUNEL signal (x -axis) is a measure of DNA fragmentation, while FSC (y-axis) is related to cell size. TUNEL-negative lymphocytes are bounded by rectangle R 1, while TUNEL-negative monocytes (CD 14 positive cells) are bounded by rectangle R2. R3 bounds the TUNEL-positive population of cells. There were minimal numbers of PI-positive cells in 6 hour samples (see Table VI).
Figure 15B:
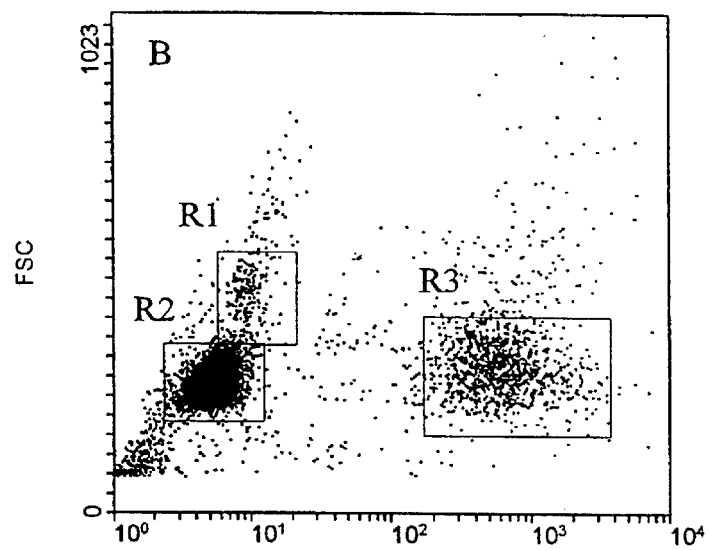
Figure 15C:
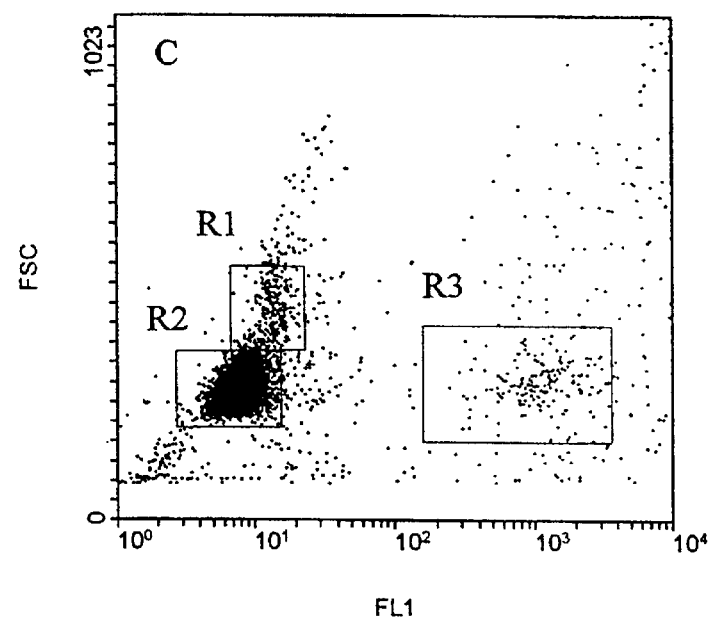

[a]Propidium iodide labels only those cells with leaky plasma membranes. Apoptotic cells do not initially have leaky plasma membranes.
[b]The TUNEL assay is used to identify cells with apoptosis-specific DNA fragmentation. TUNEL-negativecells are not apoptotic.
[c]granulocytes (polymorphonuclear cells).
[d]Monocytic leukemia cell line.
[e]Acute myeloid leukemia cell line.

in a shift of the taurolidine dose-response curve. Concentrations of taurolidine up to 200 μg/ml did not induce significant apoptosis when cells were treated in whole blood (Table VI and FIG. 15A). However, taurolidine at 500 μg/ml resulted in the appearance of a population of TUNEL-positive cells (FIG. 15B, region 3), and loss of 70% of TUNEL-negative monocytes (Table VI). As a positive control for induction of apoptosis, some cells were treated with anisomycin, a protein synthesis inhibitor known to induce apoptosis in monocytes. Anisomycin treatment of PBMC in whole blood also resulted in a loss of TUNEL-negative monocytes; however, fewer TUNEL-positive cells were detected after 6 hour incubation (FIG. 15C, region 3). There was no evidence for a significant effect of either taurolidine or anisomycin on induction of apoptosis in lymphocytes.

TABLE VI

Dose-response of PBMC (in whole blood) to Taurolidine[a]

| Treatment | % propidium iodide | % TUNEL-negative[b] |
|---|---|---|
| All cells | | |
| control | 1.4 ± 0.6 | |
| 200 μg/ml taurolidine | 1.6 ± 0.6 | |
| 500 μg/ml taurolidine | 1.4 ± 0.2 | |
| Monocytes | | |
| control | | 100 |
| 200 μg/ml taurolidine | | 117.4 ± 11.2 |
| 500 μg/ml taurolidine | | 27.9 ± 12.0 |
| Lymphocytes | | |
| control | | 100 |
| 200 μg/ml taurolidine | | 92.7 ± 6.0 |
| 500 μg/ml taurolidine | | 91.8 ± 6.9 |

[a]Analysis by flow cytometry after staining cells with PI and processing for TUNEL. Data are mean ± SD of 2 experiments.
[b]Percent of cells present in the TUNEL-negative region in control samples.

The effect of taurolidine on granulocytes was assayed by TUNEL analysis on taurolidine-treated purified granulocytes. These experiments were conducted in culture medium rather than whole blood. Granulocytes were treated with 100 μg/ml taurolidine since it had been shown that this concentration of taurolidine is apoptogenic to peripheral blood monocytes treated in culture medium. TUNEL-positive granulocytes ranged from 2% to 30% in untreated samples, and varied according to blood donor. Taurolidine treatment resulted in apoptosis of 92% of the granulocytes within 6 hours (Table VII). Therefore, the apoptogenic effect of taurolidine is not specific to monocytic cells.

TABLE VII

Response of Granulocytes to 100 μg/ml Taurolidine[a]

| granulocytes | % propidium iodide positive | % TUNEL-positive |
|---|---|---|
| control | 0.5 ± 0.2 | 17.0 ± 7.0 |
| taurolidine | 1.6 ± 0.5 | 91.5 ± 3.5 |
| vehicle | 0.5 ± 0.2 | 17.5 ± 7.0 |

[a]Analysis by flow cytometry after staining cells with PI and processing for TUNEL. Data are mean ± SEM of 5 experiments.

In another study, TUNEL assays were performed on all cell lines 6 hours after cells were initially exposed to taurolidine (cells were treated for 4 hours, rinsed, and then incubated for 2 more hours before TUNEL assay was performed).

For these experiments, the effect of 100 μg/ml taurolidine was compared to that of 1 μg/ml anisomycin, a protein synthesis inhibitor demonstrated to induce apoptosis in monocytic (Kochi, S. K. and Collier, R. J., "DNA fragmentation and cytolysis in U937 cells treated with diphtheria toxin or other inhibitors of protein synthesis," *Exp Cell Res* 208:296–302 (1993)), granulocytic (Polverion, A. J. and Patterson, S. D., "Selective activation of caspases during apoptotic induction in HL-60 cells," *J Biol Chem* 272:7013–7021 (1997)), and epithelial (Liao, et al., "Stress, apoptosis, and mitosis induce phosphorylation of human keratin 8 at Ser-73 in tissues and cultured cells," *J Biol Chem* 272:17565–17573 (1997)) cell lines. Taurolidine and anisomycin induced apoptosis in MM6, HL-60, and Jurkat cells (Table VIII). MM6 and HL-60 cells were similarly effected, with >80% TUNEL-positive cells after 6 hours. Jurkat cells were less sensitive, with approximately 50% of cells induced to undergo apoptosis after taurolidine treatment. After 6 hours, 73% of anisomycin-treated REH cells were apoptotic, with less than 20% of taurolidine-treated REH cells being TUNEL-positive. However, assay of cells 24 hours after

TABLE VIII

Response of Cell Lines to Taurolidine and Anisomycin[a]

| Cell line | % propidium iodide positive | % TUNEL-positive |
|---|---|---|
| MM6 | | |
| control | 7.3 ± 0.5 | 3.6 ± 2.6 |
| taurolidine | 22.4 ± 0.8 | 80.9 ± 7.7 |
| anisomycin | 19.1 ± 5.4 | 92.0 ± 2.3 |
| K562 | | |
| control | 2.2 ± 0.1 | 0.6 ± 0.2 |
| taurolidine | 2.2 ± 0.8 | 6.6 ± 2.8 |
| anisomycin | 4.8 ± 3.1 | 8.5 ± 8.8 |
| HL-60 | | |
| control | 3.7 ± 3.2 | 2.4 ± 0.6 |
| taurolidine | 9.1 ± 8.2 | 91.9 ± 10.9 |
| anisomycin | 28.3 ± 15.3 | 96.1 ± 6.8 |
| REH | | |
| control | 2.5 ± 0.6 | 2.8 ± 1.0 |
| taurolidine | 4.4 ± 1.6 | 18.3 ± 10.7 |
| anisomycin | 18.4 ± 0.5 | 72.9 ± 7.4 |
| Jurkat | | |
| control | 3.6 ± 0.3 | 0.6 ± 0.2 |
| taurolidine | 6.1 ± 5.8 | 51.7 ± 1.4 |

TABLE VIII-continued

Response of Cell Lines to Taurolidine and Anisomycin[a]

| Cell line | % propidium iodide positive | % TUNEL-positive |
|---|---|---|
| anisomycin | 5.1 ± 3.4 | 69.6 ± 19.8 |
| ECV304 | | |
| control | 5.6 ± 0.7 | 0.0 ± 0.0 |
| taurolidine | 2.0 ± 1.4 | 0.0 ± 0.0 |
| anisomycin | 2.2 ± 3.1 | 0.0 ± 0.0 |
| GM5387 | | |
| control | 5.7 ± 2.1 | 0.0 ± 0.0 |
| taurolidine | 5.9 ± 1.8 | 0.0 ± 0.0 |
| anisomycin | 5.4 ± 3.2 | 0.0 ± 0.0 |

[a]Analysis by flow cytometry after staining cells with propidium iodide and processing for TUNEL.
Data are percent of total cell-size events, and are expressed as mean ± SD of two experiments.
Cells were treated for 4 hours with taurolidine (100 μg/ml) or anisomycin (1 μg/ml), and then assayed at 6 hours.

treatment indicated that taurolidine does induce apoptosis in REH cells (Table IX), but that it occurs less rapidly than with anisomycin treatment, suggesting that these two agents may work by different mechanisms. K562 cells were the most resistant to apoptosis, with less than 10% TUNEL-positive cells 6 hours after treatment with either anisomycin or taurolidine. Some induction of apoptosis was demonstrated after 24 hours, with approximately 20% of taurolidine-treated K562 becoming TUNEL-positive.

Less than 0.1% of ECV304 or GM5387 cells were TUNEL-positive 6 hours after treatment with taurolidine or anisomycin (Table VIII). Therefore, neither of these agents induce rapid DNA fragmentation in these cell types. However, there was approximately a 70% increase in the number of subcellular-sized events recorded by flow cytometry after taurolidine treatment of these cells, indicating some effect of taurolidine on cell integrity. These cell fragments were not stained by propidium iodide, consistent with them being apoptotic bodies.

In summary, concentrations of taurolidine that were effective in inhibiting the induction of TF and TNFα expression in LPS-stimulated monocytic cells were also effective in inducing apoptosis in these cells. This was established by agarose gel electrophoretic analysis of DNA fragmentation MM6 cells and by TUNEL

TABLE IX

Response of Cell Lines to Taurolidine and Anisomycin: Apoptosis at 24 hours After Treatment[a]

| Cell line | % propidium iodide | % TUNEL-positive |
|---|---|---|
| K562 | | |
| control | 2.2 ± 0.3 | 0.5 ± 0.2 |
| taurolidine | 12.4 ± 2.1 | 21.2 ± 14.6 |
| anisomycin | 7.1 ± 2.3 | 2.2 ± 6.2 |
| REH | | |
| control | 3.6 ± 0.2 | 1.7 ± 1.8 |
| taurolidine | 55.8 ± 19.9 | 81.4 ± 4.4 |
| anisomycin | 51.6 ± 17.0 | 53.0 ± 2.6 |

[a]Analysis by flow cytometry after staining cells with propidium iodide and processing for TUNEL.
Data are percent of total cell-sized events, and are expressed as mean ± SD of two experiments.
Cells were treated for 4 hours with taurolidine (100 μg/ml) or anisomycin (1 μg/ml), and then assayed at 24 hours.

analysis of peripheral blood monocytes. Induction of apoptosis was relatively rapid, being detectable within four to six hours after treatment in MM6 cells and monocytes. In this time frame, DNA fragmentation was readily detectable in cells whose plasma membranes were still intact. Eventually, however, cell permeability increased (e.g., 24 hours after treatment with taurolidine). This is likely to be due to "secondary necrosis," an inevitable result of advanced in vitro apoptosis where there is no system for phagocytosis and intracellular degradation of apoptotic cells. It has now been found that taurolidine also induces apoptosis of monocytic cells treated in whole blood. The effective concentration (500 µg/ml) is 5 times that required when purified PBMC are treated in culture medium. It has been proposed that metabolites of taurolidine inactivate LPS and kills bacteria by forming cross-links between primary amine and hydroxyl groups on LPS and bacterial cell walls. (Browne, et al., "Taurolin, a new chemotherapeutic agent," *J Appl Bacteriol* 41:363–368 (1976); Pfirmann, R. W., "Taurolin: ein neues konzept zur antimikrobiellen chemotherapie chirurgischer infektionen ein fuhrung und ubersicht," In: *Taurolin, ein neues konzept zur antimikrobiellen chemotherapie chirurgischer infektionen*, edited by Brückner, W. L. and Pfirrmann, R. W., München-Wien-Baltimore: Urban and Schwarzenburg; pp. 3–23 (1985)). If taurolidine induces apoptosis by similar mechanisms, incubation in whole blood could reduce its effectiveness by providing a high concentration of non-cellular substrates. In fact, taurolidine has been reported to react with proteins in plasma and serum (Jones, et al., "A study of the stability of taurolidine in plasma and protein-free serum," *Int J Pharm* 64:R1–R4 (1990)). Taurolidine also reduces the TF activity of LPS-induced monocytes treated in whole blood, with significant reduction seen with concentrations of taurolidine as low as 200 µg/ml.

Taurolidine does not induce a significant amount of apoptosis in lymphocytes even at concentrations (in whole blood) up to 500 µg/ml. However, taurolidine is at least as effective in inducing apoptosis in granulocytes as it is in monocytes, as measured by TUNEL assays performed on purified cells treated in culture medium. It has been reported that both granulocytes and monocytes, but only a fraction of lymphocytes, constitutively express Fas antigen (Iwai, et al., "Differential expression of bcl-2 and susceptibility to anti-Fas-mediated cell death in peripheral blood lymphocytes, monocytes, and neutrophils," *Blood* 84:1201–1208 (1994)), and that cross-linking of the cell surface Fas mediates transduction of apoptotic signals into cells (Itoh, et al., "The polypeptide encoded by the cDNA for human cell surface antigen Fas can mediate apoptosis," *Cell* 66:233–243 (1991)). Although the mechanism by which taurolidine induces apoptosis is unknown, taurolidine affects monocytes and granulocytes but not lymphocytes.

Specificity of taurolidine's ability to induce apoptosis was further investigated by assessing its effects on a variety of leukemic cell lines. Taurolidine was most effective in inducing apoptosis in monocytic (MM6) and granulocytic (HL-60) leukemic cell lines, analogous to its potent effect on peripheral blood monocytes and granulocytes. However, taurolidine was also able to induce apoptosis in a significant proportion of Jurkat cells, a lymphocytic leukemia cell line. Approximately 50% of these cells became apoptotic within 6 hours of treatment. Taurolidine did not induce apoptosis in peripheral blood lymphocytes under similar experimental conditions, indicating that leukemia-derived cells may be more sensitive to taurolidine than normal cells. Taurolidine was also able to induce apoptosis in the lymphoblastic cell line REH, although the process in these cells was delayed as compared to MM6 and HL60.

As noted in previous studies (Evans, et al., "Activation of the Abelson tyrosine kinase activity is associated with suppression of apoptosis in hemopoietic cells," *Cancer Res* 53:1735–1738 (1993)), the multipotential cell line K562 was relatively resistant to apoptosis. Anisomycin induced less than 10% of these cells to become TUNEL-positive. Taurolidine was somewhat more potent, with approximately 20% of the cells becoming TUNEL-positive 24 hours after treatment was begun.

Although taurolidine inhibited proliferation of the endothelial and fibroblast cell lines, strong evidence for induction of apoptosis in these cells was not obtained. Taurolidine treatment did not cause measurable cell death, as shown by the fact that cells remained trypan blue negative throughout the 4 day culture following treatment Additionally, these cells did not demonstrate evidence for fragmentation of DNA (TUNEL positivity) when assayed 6 hours after treatment. DNA fragmentation has been used to assay for apoptosis in fibroblast cell lines (Kim, et al., "Platelet-derived growth factor induces apoptosis in growth-arrested murine fibroblasts," *Proc Natl Acad Sci* USA 92:9500–9504 (1995)) ., including, in particular, the TUNEL assay (Gansauge, et al., "The induction of apoptosis in proliferating human fibroblasts by oxygen radicals is associated with a p53- and $p21^{WAF1CIP1}$ induction," *FEBS Letters* 404:6–10 (1997)). However, some fibroblast cell lines have not exhibited DNA degradation, and apoptosis was identified by changes in cell morphology and detachment of cells from the culture vessel (Boyle, et al., "Apoptosis in C3H-10T1/2 cells: roles of intracellular pH, protein kinase C, and the Na+/H+ antiporter," *J Cell Biochem* 67:231–240 (1997)). Additionally, these studies examined cells for evidence of apoptosis 24–48 hours after treatment with the apoptogenic agent. While evidence for DNA fragmentation of fibroblast or endothelial cells was not found, analysis by flow cytometry did reveal an increase in cell fragmentation.

Taurolidine induces apoptosis in monocytes, granulocytes, and numerous leukemic cell lines. In all cells tested, it was as efficient an apoptogenic agent as the protein synthesis inhibitor anisomycin. Intravenous administration of taurolidine does not cause detectable alterations in hematologic variables, including white cell count (Browne, M. K., "Pharmacological and clinical studies with taurolin." In *Taurolin, Ein Neues Konzept zur Antimikrobiellen Chemotherapie Chirurgischer Infektionen*, Brückner, W. L. and Pfirrmann, R. W. (eds), München-Wien-Baltimore, Urban & Schwarzenberg, p. 51–60 (1985); Browne, et al., "A controlled trial of taurolin in established bacterial peritonitis," *Surg Gynecol Obstet* 146:721–724 (1978); and Williats, et al., "Effect of the antiendotoxic agent, taurolidine, in the treatment of sepsis syndrome," *Crit Care Med* 23:1033–1039 (1995)). Taurolidine provides a treatment for a variety of leukemic diseases due to its ability to induce apoptosis in leukemic cells and cells in whole blood, in conjunction with the absence of a generalized toxicity in human subjects.

Induction of apoptosis in monocytic cells by taurolidine appeared to be independent of any effects the drug may have on LPS. In fact, taurolidine induced apoptosis in monocytic cells in the absence of LPS treatment. Thus, in addition to its potential utility as a treatment for sepsis previously reported by others, we have found that taurolidine is a very effective, selective inducer of apoptosis in monocytic and myeloid cells and has utility in the treatment of certain leukemias, including monocytic and mycloid leukemias.

EXAMPLE 1

In Vitro Screening Test for Taurolidine Treatment

An in vitro screening test is performed on a patient's blood to determine if the monocytic, myeloid and/or leukemia cells would respond to taurolidine therapy by exhibiting apoptosis.

A patient's peripheral blood leukocytes are isolated from heparinized blood by centrifugation using Histopaque, Ficoll-Hypaque, or any other suitable methodology. After separation, the isolated leukocytes are suspended in RPMI+ 10% BCS. Aliquots ofthe suspended cells are treated with 10–100 μg/ml taurolidine for 4–6 hours. Cells treated with the vehicle solution alone are used as controls. The presence of apoptosis is measured as the degree of DNA fragmentation using either the agarose gel electrophoresis or the TUNEL assay. A high degree of apoptosis observed in vitro with the patient's leukemia cells is indicative of a favorable prognosis upon in vivo taurolidine treatment, while a minimal degree of apoptosis suggests alternative treatment might be preferable.

EXAMPLE 2

In Vivo Taurolidine Treatment

To decrease the number of monocytic andlor myeloid leukemia cells, a patient with monocytic and/or myeloid leukemia is treated with about 10 to 500 mg/kg body weight taurolidine administered either intravenously or intraperitoneally. The patient's response to treatment is monitored by a decrease in WBC count and examining the patient's leukocytes for a decrease in leukemia cells. Treatment can be continued as necessary.

EXAMPLE 3

In vivo Taurolidine Treatment to Reduce Coagulopathies

To decrease the hypercoagulable state associated with TF expression on circulating leukemia cells, a patient with leukemia and an associated coagulopathy is treated with about 10 to 500 mg/kg body weight taurolidine administered either intravenously or intraperitoneally. In addition, treatment can be given prior to, or concurrently with, standard cancer chemotherapy, in order to reduce the incidence or severity of thrombotic complications. The patient's response to treatment is monitored by any of a variety of standard hematologic measures of hypercoagulability or DIC. These measures include prolongation of the prothrombin time, elevated levels of fibrin degradation products (FDP), elevated levels of fibrin D-Dimer, and hypofibrinogenemia. A positive response to treatment is indicated by a return of these measures toward normal (control) levels. Treatment can be continued as necessary.

What is claimed is:

1. A method for treating a leukemia patient with taurolidine consisting essentially of the steps of administering to said patient an effective amount of taurolidine to render leukemia-causing cells in said patients apoptotic.

2. The method of claim 1, wherein said amount of taurolidine is administered intravenously.

3. The method of claim 1, wherein said amount of taurolidine is admniistered intraperitoneally.

4. The method of claim 1, wherein said effective amount of taurolidine is from about 10 to about 500 milligrams per kilogram body weight.

5. The method of claim 1, wherein said effective amount of taurolidine is about 150 milligrams per kilogram body weight.

6. A method for treating a leukemia patient with taurolidine, said patient exhibiting coagulopathy caused by TF expression on leukemia cells, comprising the steps of administering to said patient an effective amount of taurolidine to reduce coagulopathy in said patient.

7. A method of treating a leukemia patient with taurolidine, said patient exhibiting coagulopathy caused by TF expression on leukemia cells, consisting essentially of the steps of administering to said patient an effective amount of taurolidine to reduce coagulopathy in said patient.

8. The method of claim 6, wherein said amount of taurolidine is administered intraperitoneally.

9. The method of claim 6, wherein said effective amount of taurolidine is from about 10 to about 500 milligrams per kilogram body weight.

10. The method of claim 6, wherein said effective amount of taurolidine is about 150 milligrams per kilogram body weight.

11. The method of claim 7, wherein said effective amount of taurolidine is about 150 milligrams per kilogram body weight.

12. A method of rendering leukemia cells apoptotic consisting essentially of contacting said cells with an effective amount of taurolidine.

13. A method of decreasing the hypercoagulable state associated with TF expression on leukemia cells consisting essentially of contacting said cells with an effective amount of taurolidine.

* * * * *